US009018198B2

(12) United States Patent
Njar et al.

(10) Patent No.: US 9,018,198 B2
(45) Date of Patent: *Apr. 28, 2015

(54) PRODRUGS OF C-17-HETEROARYL STEROIDAL CYP17 INHIBITORS/ANTIANDROGENS: SYNTHESIS, IN VITRO BIOLOGICAL ACTIVITIES, PHARMACOKINETICS AND ANTITUMOR ACTIVITY

(71) Applicant: University of Maryland, Baltimore, Baltimore, MD (US)

(72) Inventors: Vincent Njar, Glen Burnie, MD (US); Angela Brodie, Fulton, MD (US); Lalji K. Gediya, Gaithersburg, MD (US)

(73) Assignee: University of Maryland, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/212,856

(22) Filed: Mar. 14, 2014

(65) Prior Publication Data

US 2014/0274983 A1    Sep. 18, 2014

Related U.S. Application Data

(63) Continuation of application No. 12/934,135, filed as application No. PCT/US2009/037610 on Mar. 19, 2009, now abandoned.

(60) Provisional application No. 61/039,133, filed on Mar. 25, 2008.

(51) Int. Cl.
    *A61K 31/58*    (2006.01)
    *C07J 43/00*    (2006.01)
    *A61K 45/06*    (2006.01)

(52) U.S. Cl.
    CPC .............. *C07J 43/003* (2013.01); *A61K 45/06* (2013.01); *A61K 31/58* (2013.01)

(58) Field of Classification Search
    CPC ..................................................... A61K 31/58
    USPC ......................................................... 514/176
    See application file for complete search history.

(56) References Cited

U.S. PATENT DOCUMENTS

| 4,000,125 | A | 12/1976 | Casagrande et al. |
| 5,601,981 | A | 2/1997 | Malins |
| 5,604,213 | A | 2/1997 | Barrie et al. |
| 5,994,335 | A | 11/1999 | Brodie et al. |
| 6,200,965 | B1 | 3/2001 | Brodie et al. |
| 6,444,683 | B2 | 9/2002 | Brodie et al. |
| 6,982,258 | B2 | 1/2006 | Posner et al. |
| 7,192,974 | B2 | 3/2007 | Gravestock et al. |
| 7,875,599 | B2* | 1/2011 | Brodie et al. ............. 514/176 |
| 2001/0001099 | A1 | 5/2001 | Brodie et al. |
| 2003/0054053 | A1 | 3/2003 | Young et al. |
| 2009/0012045 | A1 | 1/2009 | Hitoshi et al. |
| 2009/0047252 | A1 | 2/2009 | Cai et al. |
| 2009/0048149 | A1 | 2/2009 | Ng et al. |
| 2010/0047338 | A1 | 2/2010 | Brodie et al. |
| 2010/0048524 | A1 | 2/2010 | Brodie et al. |
| 2010/0048912 | A1 | 2/2010 | Brodie et al. |
| 2010/0048913 | A1 | 2/2010 | Brodie et al. |
| 2010/0048914 | A1 | 2/2010 | Brodie et al. |
| 2010/0137269 | A1 | 6/2010 | Brodie et al. |
| 2011/0118219 | A1 | 5/2011 | Njar et al. |

FOREIGN PATENT DOCUMENTS

| WO | WO 2005/014023 A1 | 2/2005 |
| WO | WO 2006/093993 A1 | 9/2006 |

OTHER PUBLICATIONS

Bruno, et al., 17α-Hydroxylase/17,20 Lyase Inhibitor VN/124-1 Inhibits Growth of Androgen-independent Prostate Cancer Cells via Induction of the Endoplasmic Reticulum Stress Response, Molecular Cancer Therapeutics, 7 (9), 2828-2836 (2008).*
Abstract ANIH Grant Project Reference No. 5RO1 CA27440-24, approximate date Feb. 20, 2003; approximate award date Jun. 3, 2003.
Abstract of NIH Grant Project Reference No. 2R01 CA27440-25A1, approximate submission date Feb. 18, 2004; approximate award date Sep. 23, 2004.
Abstract of NIH Grant Project Reference No. 3RO1 CA27440-22S1, approximate date Jun. 21, 2001; approximate award date Aug. 17, 2001.
Abstract of NIH Grant Project Reference No. 3RO1 CA27440-23S1, approximate date May 3, 2002; approximate award date Jun. 21, 2002.
Abstract of NIH Grant Project Reference No. 5RO1 CA27440-23, approximate date Jan. 21, 2002; approximate award date Apr. 29, 2002.
Abstract of NIH Grant Project Reference No. 5RO1 CA27440-24S1, approximate date Apr. 1, 2003; approximate award date Jun. 3, 2003.
Abstract of NIH Grant Project Reference No. 5RO1 CA27440-26, approximate submission date Jul. 1, 2005; approximate award date Aug. 2, 2005.
Abstract of NIH Grant Project Reference No. 5RO1CA27440-27, approximate submission date Apr. 26, 2006.

(Continued)

*Primary Examiner* — Erich A Leeser
(74) *Attorney, Agent, or Firm* — Wilson Sonsini Goodrich & Rosati PC

(57) ABSTRACT

Prodrugs of steroidal C-17 benzoazoles, pyrimidinoazoles (az-abenzoazoles) and diazines. Methods of synthesis are also described, whereby a prodrug group is substituted for a functional group at A ring portion of the ABC ring structure of the steroid. Suitable pro-drug groups include amino acid groups, succinate groups, phosphate groups, or sulfamate groups. The prodrugs of the disclosed compounds allow for improved oral bioavailability of the compounds that are inhibitors of human CYP 17 enzyme as well as potent antagonists of both wild type and mutant androgen receptors (AR). The compounds and the corresponding prodrugs are useful for the treatment of conditions such as human prostate cancer, breast cancer, and prostate hyperplasia.

20 Claims, 4 Drawing Sheets

(56) References Cited

OTHER PUBLICATIONS

Barrie, et al. Pharmacology of novel steroidal inhibitors of cytochrome P450(17) alpha (17 alpha-hydroxylase/C17-20 lyase). J Steroid Biochem Mol Biol. Sep. 1994;50(5-6):267-73.

Bruchovsky, et al. The conversion of testosterone to 5-alpha-androstan-17-beta-ol-3-one by rat prostate in vivo and in vitro. J Biol Chem. Apr. 25, 1968;243(8):2012-21.

Burkhart, et al. Inhibition of steroid C17(20) lyase with C-17-heteroaryl steroids. Bioorg Med Chem. Sep. 1996;4(9):1411-20.

Chen, et al. Molecular determinants of resistance to antiandrogen therapy. Nat Med. Jan. 2004;10(1):33-9.

Chengjie, et al. Synthesis of pharmacological activity of some 17-[(2'-substituted)-4'-pyramidyl] androstene derivatives as inhibitors of human 17alpha-hydroxylase/C17,20-layse. J. Chinese Pharm. Sci. 2001; 10(1):3-8.

Choshi, et al. Total synthesis of grossularines-1 and -2. J. Org. Chem. 1995; 60:5899-5904.

Clement, et al. Three dimensional pharmacophore modeling of human CYP17 inhibitors. Potential agents for prostate cancer therapy. J Med Chem. Jun. 5, 2003;46(12):2345-51.

Crawford, et al. A controlled trial of leuprolide with and without flutamide in prostatic carcinoma. New Eng J Med. 1989; 321:419-424.

Crawford, et al. Treatment of newly diagnosed stage D2 prostate cancer with leuprolide and flutamide or leuprolide alone, phase III: prognostic significance of minimal disease. J. Urol. 1992; 147:417A.

Denis. Role of maximal androgen bloackade in advanced prostate cancer. The Prostate Supplement. 1994; 5:17-22.

Denmeade, et al. A history of prostate cancer treatment. Nat Rev Cancer. 2002; 2(5):389-96.

Evans, et al. methods for drug discovery: development of potent, selective, orally effective cholecystokinin antagonists. J Med Chem 1988; 31(12):2235-46.

Grigoryev, et al. Cytochrome P450c17-expressing *Escherichia coli* as a first-step screening system for 17alpha-hydroxylase-C17,20-lyase inhibitors. Anal Biochem. Feb. 15, 1999;267(2):319-30.

Grigoryev, et al. Effects of new 17alpha-hydroxylase/C(17,20)-lyase inhibitors on LNCaP prostate cancer cell growth in vitro and in vivo. Br J Cancer. Oct. 1999;81(4):622-30.

Haidar, et al. Effects of novel 17alpha-hydroxylase/C17, 20-lyase (P450 17, CYP 17) inhibitors on androgen biosynthesis in vitro and in vivo. J Steroid Biochem Mol Biol. Apr. 2003;84(5):555-62.

Haidar, et al. Novel steroidal pyrimidyl inhibitors of P450 17 (17 alpha-hydroxylase/C17-20-lyase). Arch Pharm (Weinheim). Dec. 2001;334(12):373-4.

Hall. Cytochrome P-450 C21scc: one enzyme with two actions: hydroxylase and lyase. J Steroid Biochem Mol Biol. 1991;40(4-6):527-32.

Handratta, et al. Novel C-17-heteroaryl steroidal CYP17 inhibitors/antiandrogens: synthesis, in vitro biological activity, pharmacokinetics, and antitumor activity in the LAPC4 human prostate cancer xenograft model. J Med Chem. Apr. 21, 2005;48(8):2972-84.

Handratta, et al. Potent CYP17 inhibitors: improved syntheses, pharmacokinetics and anti-tumor activity in the LNCaP human prostate cancer model. J Steroid Biochem Mol Biol. Oct. 2004;92(3):155-65.

Hartmann, et al. Synthesis and evaluation of novel steroidal oxime inhibitors of P450 17 (17 alpha-hydroxylase/C17-20-lyase) and 5 alpha-reductase types 1 and 2. J Med Chem. Nov. 2, 2000;43(22):4266-77.

Huggins, et al. Studies in prostate cancer: The effects of castration on advanced carcinoma of the prostate gland. Arch Surg. 1941; 43(2):209-223.

Humber, et al. Synthesis and biological activity of some cardiotonic compounds related to digitoxigenin. Steroids. Aug. 1983;42(2):189-202.

International search report dated Oct. 7, 2009 for PCT/US2009/036891.

International search report dated Dec. 9, 2009 for PCT/US2009/037610.

Jarman, et al. Inhibitors of enzymes of androgen biosynthesis: cytochrome P450(17) alpha and 5 alpha-steroid reductase. Nat Prod Rep. Oct. 1998;15(5):495-512.

Jarman, et al. The 16,17-double bond is needed for irreversible inhibition of human cytochrome p45017alpha by abiraterone (17-(3-pyridyl)androsta-5, 16-dien-3beta-ol) and related steroidal inhibitors. J Med Chem. Dec. 31, 1998;41(27):5375-81.

Jefcoate. Measurement of substrate and inhibitor binding to microsomal cytochrome P-450 by optical-difference spectroscopy. Methods Enzymol. 1978;52:258-79.

Jemal, et al. Cancer statistics, 2004. CA cancer J. Clin. 2004; 54(1):8-29.

Kadar, et al. Technical and safety aspects of blood and marrow transplantation using G-CSF mobilized family donors. Transfus Sci. Dec. 1996;17(4):611-8.

Kim, et al. Synergism of cytoplasmic kinases in IL6-induced ligand-independent activation of androgen receptor in prostate cancer cells. Oncogene. Mar. 11, 2004;23(10):1838-44.

Klein, et al. Progression of metastatic human prostate cancer to androgen independence in immunodeficient SCID mice. Nat Med. Apr. 1997;3(4):402-8.

Ling, et al. 17-Imidazolyl, pyrazolyl, and isoxazolyl androstene derivatives. Novel steroidal inhibitors of human cytochrome C17,20-lyase (P450(17 alpha). J Med Chem. Sep. 26, 1997;40(20):3297-304.

Long, et al. Antiandrogenic effects of novel androgen synthesis inhibitors on hormone-dependent prostate cancer. Cancer Res. Dec. 1, 2000;60(23):6630-40.

Matsunaga, et al. C17,20-lyase inhibitors I. Structure-based de novo design and SAR study of C17,20-lyase inhibitors. Bioorg Med Chem. May 1, 2004;12(9):2251-73.

Matsunaga, et al. Synthetic studies on (1S)-1-(6,7-dimethoxy-2-naphthyl)-1-(1H-imidazol-4-yl)-2-methylpropan-1-ol as a selective C17,20-lyase inhibitor. Tetrahedron: Asymmetry. 2004; 15:2021-2028.

Matsunaga, et al. C(17,20)-lyase inhibitors. Part 2: design, synthesis and structure-activity relationships of (2-naphthylmethyl)-1H-imidazoles as novel C(17,20)-lyase inhibitors. Bioorg Med Chem. Aug. 15, 2004;12(16):4313-36.

McConnell. Physiologic basis of endocrine therapy for prostatic cancer. Urol Clin North Am. Feb. 1991;18(1):1-13.

Mohler, et al. The androgen axis in recurrent prostate cancer. Clin Cancer Res. Jan. 15, 2004;10(2):440-8.

Muscato, et al. Optimal dosing of ketoconazole (KETO) and hydrocortisone (HC) leads to long responses in hormone refractory prostate cancer. Proc ASCO. 1994; 229:701.

Nicolaou, et al. Natural Product-like Combinatorial Libraries Based on Privileged Structures. 1. General Principles and Solid-Phase Synthesis of Benzopyrans. J. Am. Chem. Soc. 2000; 122(41):9939-9953.

NIH Grant Project Reference No. 2RO1 CA27440-24A1, 2R01 CA27440-25A1 Revised Grant Renewal Application, approximate submission date Feb. 18, 2004; approximate award date Sep. 23, 2004.

NIH Grant Project Reference No. 3R)1 CA27440-22S1 Grant Application for Supplemental Funding, approximate date Jun. 21, 2001; approximate award date Aug. 17, 2001.

NIH Grant Project Reference No. 3RO1 CA27440-22S1 Grant Application for Supplemental Funding, approximate date Jun. 21, 2001; approximate award date Aug. 17, 2001.

NIH Grant Project Reference No. 3RO1 CA27440-23S1 Grant Continuation Application and Progress Report, approximate date May 3, 2002; approximate award date Jun. 21, 2002.

NIH Grant Project Reference No. 5R)1 CA27440-24S1 Grant Continuation Application and Progress Report, approximate date Apr. 1, 2003; approximate award date Jun. 3, 2003.

NIH Grant Project Reference No. 5RO1 CA27440-23 Grant Continuation Application and Progress Report, approximate date Jan. 21, 2002; approximate award date Apr. 29, 2002.

NIH Grant Project Reference No. 5RO1 CA27440-24 Grant Continuation Application and Progress Report, approximate date Feb. 20, 2003; approximate award date Jun. 3, 2003.

NIH Grant Project Reference No. 5RO1 CA27440-24S1 Grant Continuation Application and Progress Report, approximate date Apr. 1, 2003; approximate award date Jun. 3, 2003.

(56) References Cited

OTHER PUBLICATIONS

NIH Grant Project Reference No. 5RO1 CA27440-25 Grant Renewal Application, approximate submission date Jun. 26, 2003 —Unfunded.

NIH Grant Project Reference No. 5RO1 CA27440-26 Grant Continuation Application and Progress Report, approximate submission date Jul. 1, 2005; approximate award date Aug. 2, 2005.

NIH Grant Project Reference No. 5RO1 CA27440-27 Grant Continuation Application and Progress Report, approximate submission date Apr. 26, 2006.

NIH Grant Project Reference No. 5RO1CA27440-27 ESNAP Report, approximate submission date May 8, 2006.

Njar, et al. Inhibitors of 17alpha-hydroxylase/17,20-lyase (CYP17): potential agents for the treatment of prostate cancer. Curr Pharm Des. Mar. 1999;5(3):163-80.

Njar, et al. Novel 17-azolyl steroids, potent inhibitors of human cytochrome 17 alpha-hydroxylase-C17,20-lyase (P450(17) alpha): potential agents for the treatment of prostate cancer. J Med Chem. Mar. 12, 1998;41(6):902-12.

Njar, et al. Nucleophilic vinylic 'Addition-Elimination' Substitution Reaction of 3B-Acetoxy-17-Chloro-16-Formylandrosta-5,16-Diene: A Novel and General Route to 17-Substituted Steroids Bioorganic and Medical Chemistry Letters 1996; 6(22):2777-27820.

Nnane, et al. Effects of novel 17-azolyl compounds on androgen synthesis in vitro and in vivo. J Steroid Biochem Mol Biol. Dec. 15, 1999;71(3-4):145-52.

O'Donnell, et al. Hormonal impact of the 17alpha-hydroxylase/C(17,20)-lyase inhibitor abiraterone acetate (CB7630) in patients with prostate cancer. Br J Cancer. Jun. 14, 2004;90(12):2317-25.

Office Action dated Jan. 31, 2011 for U.S. Appl. No. 12/577,094.
Office Action dated Feb. 28, 2013 for U.S. Appl. No. 12/934,135.
Office Action dated Mar. 12, 2010 for U.S. Appl. No. 11/817,550.
Office Action dated May 5, 2010 for U.S. Appl. No. 12/577,091.
Office Action dated May 7, 2010 for U.S. Appl. No. 12/577,092.
Office Action dated May 23, 2011 for U.S. Appl. No. 12/577,094.
Office Action dated May 25, 2010 for U.S. Appl. No. 12/577,096.
Office Action dated Jun. 1, 2010 for U.S. Appl. No. 12/577,090.
Office Action dated Jun. 1, 2011 for U.S. Appl. No. 12/623,257.
Office Action dated Jun. 2, 2010 for U.S. Appl. No. 11/817,550.
Office Action dated Sep. 8, 2011 for U.S. Appl. No. 12/577,096.
Office Action dated Sep. 9, 2011 for U.S. Appl. No. 12/577,090.
Office Action dated Sep. 16, 2013 for U.S. Appl. No. 12/934,135.
Office Action dated Oct. 20, 2010 for U.S. Appl. No. 12/623,257.
Office Action dated Oct. 28, 2010 for U.S. Appl. No. 12/577,091.
Office Action dated Oct. 28, 2010 for U.S. Appl. No. 12/577,092.
Office Action dated Oct. 29, 2010 for U.S. Appl. No. 12/577,090.
Office Action dated Nov. 1, 2010 for U.S. Appl. No. 12/577,096.

Ojida, et al. Stereocontrolled synthesis of (1S)-1-(1H-imidazol-4-yl)-1-(6-methoxy-2-naphthyl)-2-methylpropan-1-ol as a potent C17,20-lyase inhibitor. Tetrahedron: Asymmetry. 2004; 15L1555-1559.

Picard, et al. Synthesis and evaluation of 2'-substituted 4-(4'-carboxy- or 4'-carboxymethylbenzylidene)-N-acylpiperidines: highly potent and in vivo active steroid 5alpha-reductase type 2 inhibitors. J Med Chem. Aug. 1, 2002;45(16):3406-17.

Potter, et al. A convenient, large-scale synthesis of abiraterone acetate [3B-acetoxy-17-(3-pryidyl)androsta-5,16-diene], a potential new drug for the treatment of prostate cancer. Organic Preparations and Procedures Int. 1997; 29(1):123-134.

Potter, et al. Novel steroidal inhibitors of human cytochrome P45017 alpha (17 alpha-hydroxylase-C17,20-lyase): potential agents for the treatment of prostatic cancer. J Med Chem. Jun. 23, 1995;38(13):2463-71.

Randimbivololona, et al. Metabolism and excretion in bile of SC4453, a new semi-synthetic derivative of digoxin following an i.v. bolus injection in the guinea-pig. J Pharmacol. Jan.-Mar. 1984;15(1):53-64.

Recanatini, et al. A new class of nonsteroidal aromatase inhibitors: design and synthesis of chromone and xanthone derivatives and inhibition of the P450 enzymes aromatase and 17 alpha-hydroxylase/C17,20-lyase. Med Chem. Mar. 1, 2001;44(5):67280.

Ru, et al. Synthesis and Pharmacological Activity of some 17-[2'substituted)-4'-pyrimidyl]androstene derivativies as inhibitors of human 17alpha-hydroxylase/C17,20-lyse., J. Chin. Pharm. Sci., Jun. 2001, vol. 10, No. 1, pp. 3-8.

Small, et al. Ketoconazole retains activity in advanced prostate cancer patients with progression despite flutamide withdrawal. J Urol. Apr. 1997;157(4):1204-7.

Souillac, et al. Characterization of Delivery Systems, Differential Scanning Calorimetry in Encyclopedia of Controlled Drug Delivery, 1999, John Wiley & Sons, pp. 212-227.

Supplementary European Search Report dated Jul. 29, 2009 for European Application No. EP 06736460.

Thompson, et al. Androgen antagonist activity by the antioxidant moiety of vitamin E,2,2,5,7,8-pentamethyl-6-chromanol in human prostate carcinoma cells. Mol Cancer Ther. Aug. 2003;2(8):797-803.

Tindall, et al. Symposium on androgen action in prostate cancer. Cancer Res. Oct. 1, 2004;64(19):7178-80.

Trachtenberg, et al. Ketoconazole: a novel and rapid treatment for advanced prostatic cancer. J Urol. Jul. 1983;130(1):152-3.

Vasaitis, et al. Androgen Receptor Inactivation Contributes to Antitumor Efficacy of CYP17 Inhibitor VN/124-1 in Prostate Cancer. Mol. Cancer Therapeutics. 2008; 7(8):2348-2357.

Vasaitis, et al. The Effects of Novel Anti-Androgens on Androgen Receptor Action and Expression. Proceedings of the American Association for Cancer Research. 2006; 47:Abstract 5340. http://aacrmeetingabstracts.org/cgi/content/abstract/2006/1/252-d.

Vippagunta, et al. Crystalline solids. Adv Drug Deliv Rev. May 16, 2001;48(1):3-26.

Voets, et al. Heteroaryl-substituted naphthalenes and structurally modified derivatives: selective inhibitors of CYP11B2 for the treatment of congestive heart failure and myocardial fibrosis. J Med Chem. Oct. 20, 2005;48(21):6632-42.

Zhang, et al. A small composite probasin promoter confers high levels of prostate-specific gene expression through regulation by androgens and glucocorticoids in vitro and in vivo. Endocrinology. Dec. 2000;141(12):4698-710.

Office Action dated Apr. 4, 2012 for U.S. Appl. No. 12/577,090.
Office Action dated Oct. 5, 2011 for U.S. Appl. No. 12/577,094.
Office Action dated Oct. 17, 2012 for U.S. Appl. No. 12/577,090.

* cited by examiner

PRODRUGS OF C-17-HETEROARYL STEROIDAL CYP17 INHIBITORS/ANTIANDROGENS: SYNTHESIS, IN VITRO BIOLOGICAL ACTIVITIES, PHARMACOKINETICS AND ANTITUMOR ACTIVITY

CROSS-REFERENCE

This application is a continuation application of U.S. patent application Ser. No. 12/934,135, filed on Feb. 2, 2011, which claims the benefit of PCT Application No. PCT/US2009/037610, filed on Mar. 19, 2009, which claims the benefit of U.S. Provisional Application No. 61/039,133, filed on Mar. 25, 2008, all of which are incorporated herein by reference in their entirety.

STATEMENT AS TO FEDERALLY SPONSORED RESEARCH

This invention was made with government support under Grant Number CA027440 awarded by the National Institutes of Health. The government has certain rights in the invention.

BACKGROUND OF THE INVENTION

This invention relates generally to chemical entities, particularly steroidal C-17 benzoazoles, pyrimidinoazoles (azabenzoazoles) and diazines and, more particularly, to prodrugs of these entities. The invention also includes methods for the synthesis of the prodrugs of the steroidal C-17 benzoazoles, pyrimidinoazoles and diazines, and the use of the prodrugs in treating diseases and conditions such as cancer.

Prostate cancer (PCA) is the most common malignancy and age-related cause of cancer death worldwide. Apart from lung cancer, PCA is the most common form of cancer in men and the second leading cause of death in American men. In the United States in 2008, an estimated 186,320 new case of prostate cancer will be diagnosed and about 28,660 men will die of this disease, with African American men and Jamaican men of African decent having the highest incidence rates in the world[1]. Androgens play an important role in the development, growth, and progression of PCA[2]. The two most important androgens in this regard are testosterone (T) and dihydrotestosterone (DHT). The testes synthesize about 90% of T and the rest (10%) is synthesized by the adrenal glands. T is further converted to the more potent androgen DHT by the enzyme steroid 5α-reductase that is localized primarily in the prostate[3]. Huggins et al. introduced androgen deprivation as therapy for advanced and metastatic PCA in 1941[4]. Thereafter, androgen ablation therapy has been shown to produce the most beneficial responses in multiple settings in PCA patients[5]. Orchidectomy (either surgical or medical with a GnRH agonist) remains the standard treatment option for most prostate cancer patients. Medical and surgical orchidectomy reduces or eliminates androgen production by the testes but does not affect androgen synthesis in the adrenal glands. Several studies have reported that a combination therapy of orchidectomy with antiandrogens, to inhibit the action of adrenal androgens, significantly prolongs the survival of PCA patients[6-8]. In a recent featured article by Mohler and colleagues,[9] it was clearly demonstrated that T and DHT occur in recurrent PCA tissues at levels sufficient to activate androgen receptor. In addition, using microarray-based profiling of isogenic PCA xenograft models, Sawyers and colleagues[10] found that a modest increase in androgen receptor mRNA was the only change consistently associated with the development of resistance to antiandrogen therapy. Potent and specific compounds that inhibit androgen synthesis in the testes, adrenals, and other tissue may be more effective for the treatment of PCA[11].

In the testes and adrenal glands, the last step in the biosynthesis of T involves two key reactions, which act sequentially and they are both catalyzed by a single enzyme, the cytochrome P450 monooxygenase 17α-hydroxylase/17,20-lyase (CYP17)[12]. Ketoconazole, an antifungal agent, and by virtue of inhibiting P450 enzymes is also a modest CYP17 inhibitor, and has been used clinically for the treatment of PCA[13]. It is reported that careful scheduling of treatment can produce prolonged responses in otherwise hormone-refractory prostate cancer patients[14]. Furthermore, ketoconazole was found to retain activity in advanced PCA patients with progression despite flutamide withdrawal[15]. Although, ketoconazole has now been withdrawn from use because of liver toxicity and other side effects this suggests that more potent and selective inhibitors of CYP17 could provide useful agents for treating this disease, even in advanced stages and in some patients who may appear to be hormone refractory.

A variety of potent steroidal and non-steroidal inhibitors of CYP17 have been reported and some have been shown to be potent inhibitors of testosterone production in rodent models[11]. Recently, Jarman and colleagues have described the hormonal impact of their most potent CYP17 inhibitor, abiraterone in patients with prostate cancer[16]. Some of our potent CYP17 inhibitors have been shown to also inhibit 5α-reductase and/or are potent antiandrogens with potent antitumor activity1. Further illustrative of the background of the invention are U.S. Pat. Nos. 5,994,335; 6,200,965; and, 6,444,683.

SUMMARY OF THE INVENTION

This invention provides prodrugs of steroidal C-17 benzoazoles, pyrimidinoazoles (azabenzoazoles) and diazines. Methods of synthesis are also described, whereby a prodrug group is substituted for a functional group at the A ring portion of the ABC ring structure of the steroid. Suitable prodrug groups include amino acid groups, succinate groups, phosphate groups, or sulfamate groups. The prodrugs of the disclosed compounds allow for improved oral bioavailability of the compounds that are inhibitors of human CYP17 enzyme as well as potent antagonists of both wild type and mutant androgen receptors (AR). The compounds and the corresponding prodrugs are useful for the treatment of conditions such as human prostate cancer, breast cancer, and prostate hyperplasia.

BRIEF DESCRIPTION OF THE DRAWINGS

FIG. 2A is a qRT-PCR assessment of stress response and cell cycle related genes in PC-3 cells following 24 hr exposure to 20 μM VN/124-1. Expression is measured as fold change relative to control. FIG. 2B includes representative western blots following 6 and 24 hour treatment with Compound 5, 500 nM of the known ERSR-inducer thapsigargin (Thaps.), or 20 µM DHA in PC-3. Numbers under the panels represent the mean fold change relative to control as measured by densitometry. FIG. 2C illustrates the effect of 20 µM Compound 5 on cell cycle progression. PC-3 cells were synchronized in G1/G0 by serum starvation for 96 hrs. Cells were then incubated with full growth medium containing either vehicle or 20 µM VN/124-1, and cell cycle was assessed at relative timepoints by flow cytometry. All graphs represent the mean±SEM of three independent experiments. *p<0.05, p<0.01, *p<0.001

DETAILED DESCRIPTION OF THE INVENTION

Figure 1A:
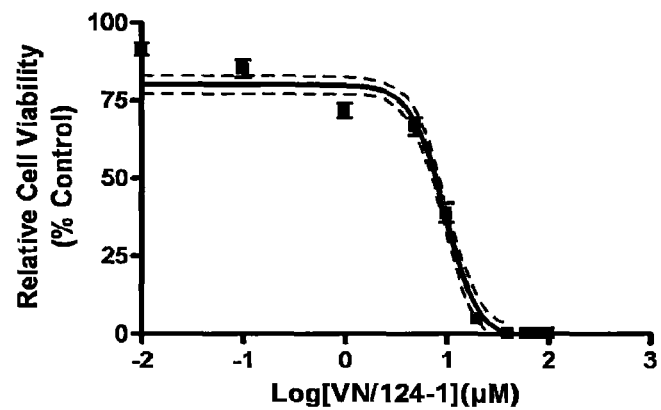
FIGS. 1A-C include cell viability curves for PC-3 (FIG. 1A), DU-145 (FIG. 1B), and LNCaP (FIG. 1C) generated from an MTT assay after 96 hour exposure to Compound 5 as described in the Examples. Data points represent the mean±SEM of 18 replicates from three independent experiments. The solid line is a best fit sigmoidal-dose response (variable slope) and dotted lines represent the 95% confidence interval.

WO 2006/093993, hereby incorporated by reference, discloses a series of potent CYP17 inhibitors/antiandrogens, the 17-benzoazoles, 17-pyrimidinoazoles and 17-diazines. These compounds are potent inhibitors of human CYP17 enzyme as well as potent antagonist of both wild type and mutant androgen receptors (AR). Particularly potent CYP17 inhibitors, referring to Schemes 1 and 2, were 3β-hydroxy-17-(1H-benzimidazole-1-yl)androsta-5,16-diene (Compound 5, code named VN/124-1), 3β-hydroxy-17-($5^1$-pyrimidyl)androsta-5,16-diene (Compound 15), 17-(1H-benzimidazole-1-yl)androsta-4,16-diene-3-one (Compound 6), with $IC_{50}$ values of 300, 500 and 915 nM, respectively. Compounds 5, 6, 14 and 15 were effective at preventing binding of $^3$H-R1881 (methyltrienolone, a stable synthetic androgen) to both the mutant and LNCaP AR and the wild-type AR, but with a 2.2 to 5-fold higher binding efficiency to the latter. Compounds 5 and 6 were also shown to be potent pure AR antagonists. The cell growth studies showed that Compounds 5 and 6 inhibit the growth of DHT-stimulated LNCaP and LAPC4 prostate cancer cells with $IC_{50}$ values in the low micromolar range (i.e., <10 µM). Their inhibitory potencies were comparable to that of casodex but remarkably superior to that of flutamide. The pharmacokinetics of Compounds 5 and 6 in mice was investigated. Following s.c. administration of 50 mg/kg of Compounds 5 and 6, peak plasma levels of 16.82 and 5.15 ng/mL, respectively occurred after 30 to 60 min, both compounds were cleared rapidly from plasma (terminal half-lives of 44.17 and 39.93 min, respectively) and neither was detectable at 8 hours. Remarkably, Compound 5 was rapidly converted into a metabolite tentatively identified as 17-(1H-benzimidazol-1-yl)androsta-3-one. When tested in vivo, Compound 5 proved to be very effective at inhibiting the growth of androgen-dependent LAPC4 human prostate tumor xenograft, while Compound 6 was ineffective. Compound 5 (50 mg/kg/twice daily) resulted in a 93.8% reduction (P=0.00065) in the mean final tumor volume compared with controls, and it was also significantly more effective than castration. To our knowledge, this was the first example of an anti-hormonal agent (an inhibitor of androgen synthesis (CYP17 inhibitor)/antiandrogen) that is significantly more effective than castration in suppression of androgen-dependent prostate tumor growth. In view of these impressive anti-cancer properties, Compound 5 and others can be used for the treatment of human prostate cancer, as well as breast cancer, ovarian cancer, and other urogenital cancers or other androgen-related conditions or diseases.

High oral bioavailability is often an important consideration for the development of bioactive molecules as therapeutic agents. Some molecular properties that influence the oral bioavailability of drug candidates were determined using ChemDraw 3D Ultra 8.0 and Chemaxon Marvin programs. Using this approach, the properties of Compound 5, for example, satisfies both the Lipinski "rule of five"[18] and the recently discovered new rule by Veber et al.,[19] for predicting an improved likelihood of high or drug-like oral bioavailability for new drug candidates. These findings for Compound 5 are presented in Table 1, and suggest that the compound should be highly orally bioavailable and as such is a strong drug candidate.

TABLE 1

Molecular Properties of Compound 5 (VN/124-1) Based on Lipinski's and Verber's Criteria

|  | Limit | VN/124-1 | Results |
| --- | --- | --- | --- |
| A. Lipinski Criterion | | | |
| Hydrogen bond donors | ≤5 | 1 | Pass |
| Hydrogen bond acceptors | ≤10 | 2 | Pass |
| Molecular weight | ≤500 | 388.2515 | Pass |
| CLogP | <5 | 5.822 | Fail |
| B. Veber's Criterion | | | |
| Number of rotatable bonds | ≤10 | 1 | Pass |
| Polar surface area | ≤140° $A^2$ | 38.05° $A^2$ | Pass |
| Sum of hydrogen bond donors and acceptors | ≤12 | 3 | Pass |

However, some further studies have found that Compound 5 has low (~10%) oral bioavailability in rat. On the basis of the Lipinski's rule, Compound 5 has higher cLog P value (i.e. >5), which could be the major reason for the finding of poor oral bioavailability. Because oral administrations of drugs are generally preferred, it is important to find ways to improve the oral bioavailability of Compound 5, as well as the other compounds of WO 2006/093993. To achieve this goal, the present invention utilizes a prodrug approach to increase bioavailability. As used herein, references to "prodrug" are to be understood to refer to a modified version or precursor of a parent compound, designed to enhance delivery properties and be converted to the parent compound in the body.

The general object of the invention can be attained, at least in part through C-17 heteroaryl steroid compounds of the following general formula I:

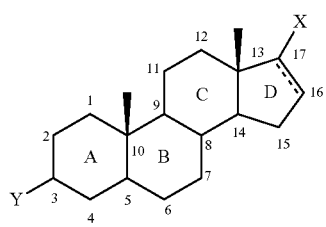

wherein:

the ABC ring structure is the A, B and C ring portions of a steroid or analog thereof, which are optionally substituted;

the ⎓ bond at the 16,17 position is a double bond or, when the compound is 17-(1H-benzimidiazol-1-yl)-androst-3-one, a single bond;

X is an optionally substituted benzimidazole, benzotriazole, pyrimidinoimidazole, pyrimidinotriazole, diazole, triazole, or diazine; the benzimidazole, benzotriazole, and pyrimidinoimidazole groups being bonded to the steroid residue through a nitrogen atom on the 5-membered ring; and, the diazole, triazole, or diazine groups being bonded to the steroid residue through a carbon atom or nitrogen on the diazole, triazole, or diazine ring; and Y is an amino acid group, a succinate group, a phosphate group, or a sulfamate group. Pharmaceutically acceptable salts of these compounds are also included in this invention.

The optional substitution for the ABC ring structure includes one or more of: alkyl and halogenated alkyl (preferably $C_{1-6}$); alkenyl and halogenated alkenyl (preferably $C_{1-6}$) including where the double bond is directly attached to the ring structure; halogen; amino; aminoalkylene; hydroxyimino; and hydroxy. Further optionally, hydrogen substituents on adjacent carbon atoms of the ABC ring structure may be removed and replaced by an additional bond between the adjacent carbon atoms to result in a double bond between these carbons in the ring structure. Preferred optional substitutions on the ABC ring structure are methyl groups at the 10 and/or 13 positions of the ring structure.

The optional substitution for the benzimidazole, benzotriazole, pyrimidinoimidazole, pyrimidinotriazole, diazole, triazole, or diazine structures include halogen, amino, aminoalkylene, hydroxy, —SH, —S-alkyl, alkyl and halogenated alkyl (preferably $C_{1-6}$). These optional substituents will desirably be on ring carbon atoms of the benzimidazole, benzotriazole, pyrimidinoimidazole, pyrimidinotriazole, diazole, triazole, or diazine structures.

Exemplary benzimidazole, benzotriazole, pyrimidinoimidazole, diazole, triazole, pyrimidinotriazole, or diazine structures are of the following formulae, respectively:

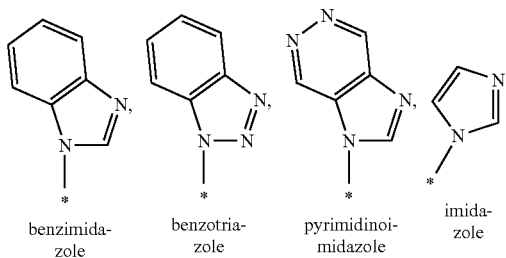

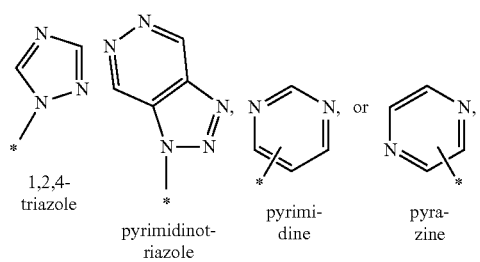

wherein the * indicates the point of attachment to the steroid residue.

In one preferred embodiment, the ABC ring structure has a C ring which has no substitution except for preferably alkyl, particularly methyl, substitution at the carbon shared with the D ring which is adjacent the attachment to the C-17 heteroaryl substitution, i.e., the 13-position.

Examples of optional substituents for the heteroaryl ring, X, are shown by the following structures wherein X is benzimidazole. Analogous compounds wherein X is substituted benzotriazole, pyrimidinoimidazole, pyrimidinotriazole, diazole, triazole, diazine, pyrazine, or pyrimidine are also contemplated.

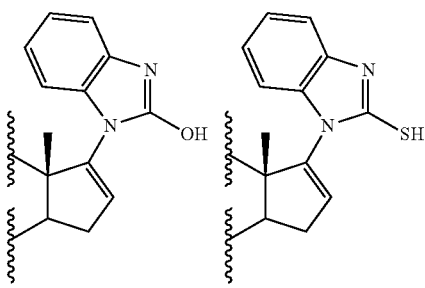

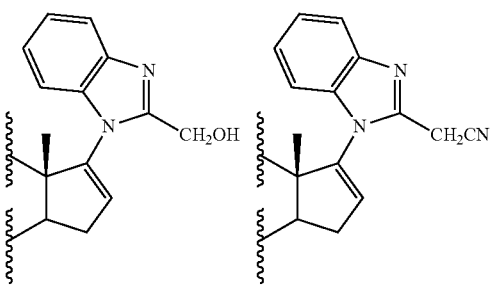

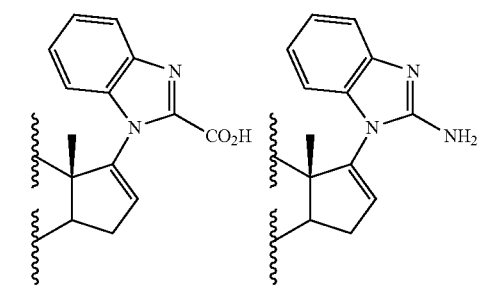

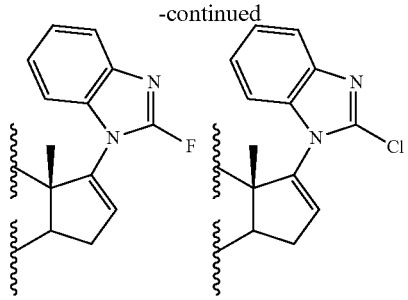
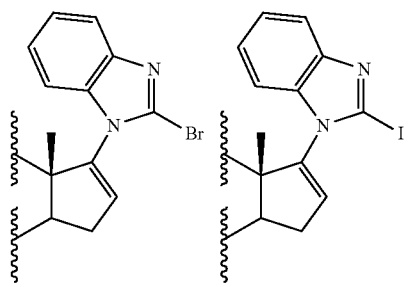
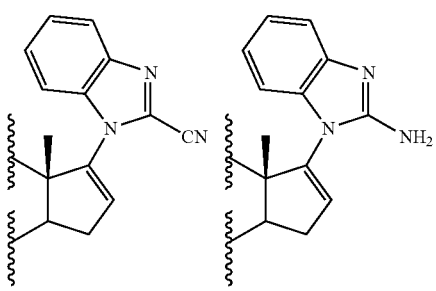
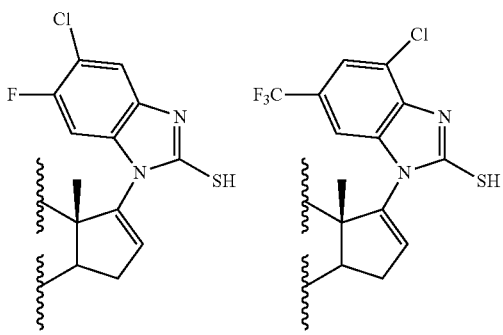
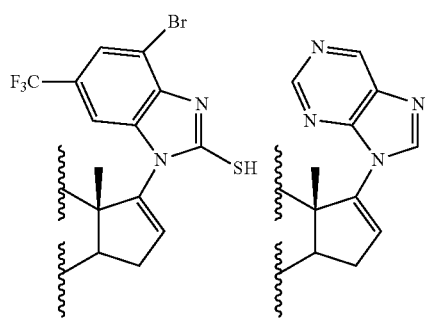

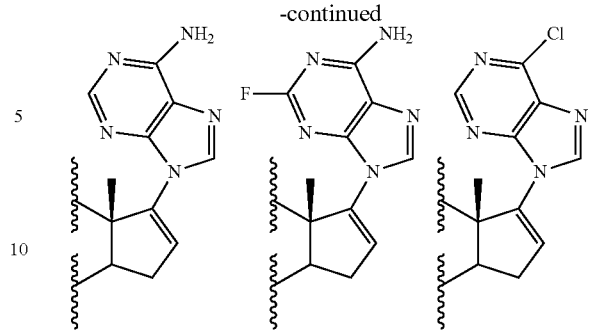
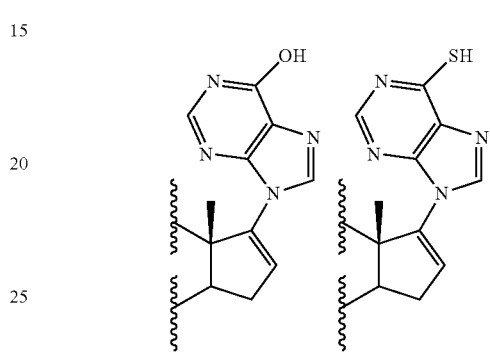

Other examples of optional substituents for the heteroaryl ring, X, are shown by the following structures wherein X is substituted C-17-azabenzimidazole (i.e., pyrimidinoimidazole or purine). Analogous compounds wherein X is substituted benzimidazole, benzotriazole, pyrimidinotriazole, triazole, pyrazine, or pyrimidine are also contemplated.

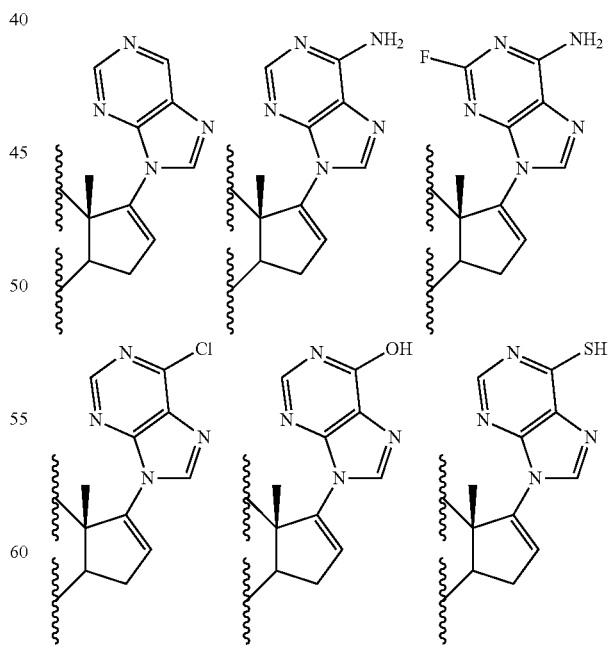

Particularly preferred compounds for use as a prodrug of this invention include those of the following structures.

Compound 5
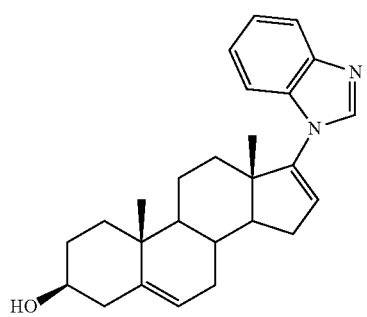

Compound 6
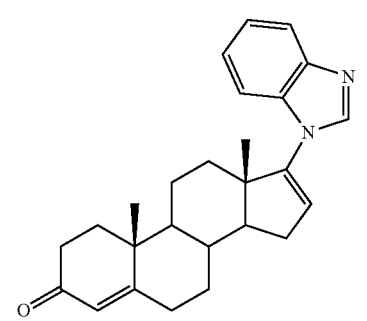

Compound 9
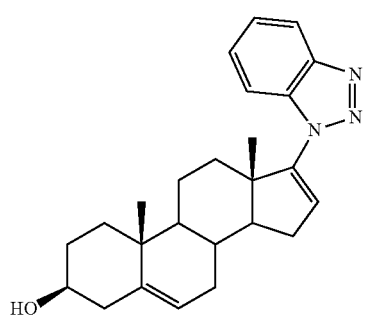

Compound 10
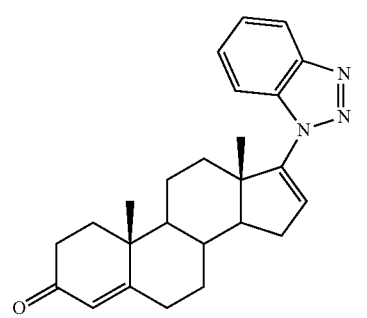

Compound 16
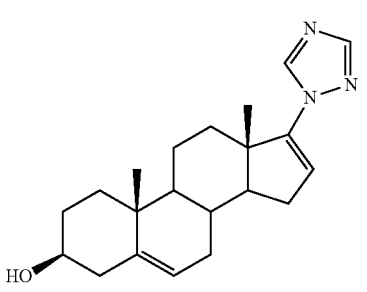

-continued

Compound 17
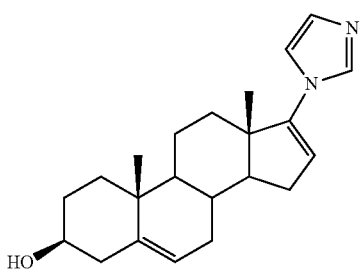

The following lists the chemical names of the above compounds.

Compound 5: 3β-Hydroxy-17-(1H-benzimidazole-1-yl)androsta-5,16-diene

Compound 6: 17-(1H-Benimidazole-1-yl)androsta-4,16-diene-3-one

Compound 9: β3-Hydroxy-17-(benzo-1H-1,2,3-triazole-1-yl)androsta-5,16-diene

Compound 10: 17-(Benzo-1H-1,2,3-triazol-1-yl)androsta-4,16-diene-3-one

Compound 16: β3-Hydroxy-17-(1H-1,2,4-triazol-1-yl)androsta-5,16-diene

Compound 17: β3-Hydroxy-17-(1H-imidazol-1-yl)androsta-5,16-diene

The inhibitory activities of these compounds versus CYP17 and steroid 5α-reductases, the binding to and transactivation of androgen receptors, and their antiproliferative effects against two human prostate cancer cell lines, LNCaP and LAPC-4 were studied and reported in WO 2006/093993. WO 2006/093993 also reported the evaluation of the pharmacokinetics of Compounds 5 and 6 of Scheme 1 in mice and the in vivo antitumor activities against human LAPC-4 prostate carcinoma in mice.

The preparation of the new 17-benzoazoles and 17-diazines is outlined in Schemes 1 and 2, respectively. These methods can be applied analogously to other analogs described herein.

The key intermediate in the synthesis of the 17-benzazoles, 3β-acetoxy-17-chloro-16-formylandtrosta-5,16-dine (2) was obtained by the routine procedure as previously described[21,22] (Scheme 1). Treatment of Compound 2 with benzimidazole in the presence of $K_2CO_3$ in DMF at approx. 80° C. gave the desired β3-acetoxy-17-1H-benzimidazole (3) in near quantitative yield. Compound 3 was smoothly deformylated with 10% palladium on activated charcoal in refluxing benzonitrile to give Compound 4 in 93% yield, from which hydrolysis gave the required 3β-hydroxy 17-benzimidazole (5). Modified Oppenauer oxidation of Compound 5 afforded the corresponding $\Delta^4$-3-oxo analog (6).

The reaction of Compound 2 with benzotriazole in the presence of $K_2CO_3$ in DMF at approximately 80° C. gave the desired 3β-acetoxy-17-benzo-1H-1,2,3-triazole 7b in excellent yield, together with the 2H-1,2,3-triazole regioisomer 7a in approximately 5% yield. These two regioisomers were readily separated by flash column chromatography (FCC) on silica gel and were also easily identified by their respective proton NMR spectra. Thus, the four aromatic protons of the symmetrical 2H-1,2,3-triazole 7a appeared as two pairs of doublets at δ 7.43, 7.45, 7.88 and 7.90 while the four aromatic protons of the unsymmetrical 1H-1,2,3-triazole 7b appeared as multiplet at δ 7.46 (2H) and doublets at δ 7.57 (1H) and 8.15 (1H), respectively. In addition, the 16-CHO proton in Compound 7a was significantly shifted downfield to δ 10.66 compared to that in Compound 7b at δ 9.59. Deformylation of Compound 7b with in situ generation of Rh(1,3-bis(diphenylphosphino)propane)$_2^+$Cl$^-$ catalyst [Rh(dppp)$_2^+$Cl$^-$] in refluxing xylenes gave compound 8, and following hydrolysis of the 3β-acetoxy group, we obtained the target 3β-hydroxy-17-(benzo-1H-1,2,3-triazol-1-yl)androsta-5,16-diene (9) in 90% yield. Oxidation of Compound 9 afforded Compound 10 in good yield.

Synthesis of the 17-diazines, (17-diazine 14 and 17-pyrimidine 15) commenced from the readily available dehydroepiandrosterone (Compound 11, Scheme 2), which was converted to the corresponding 17 hydrazone 12 by treatment with hydrazine hydrate and hydrazine sulfate as previously described by Potter et al.[22] Treatment of Compound 12 with iodine in the presence of 1,1,3,3-tetramethylguanidine gave the vinyl 17-iodide 13 in excellent yield. The palladium catalyzed cross-coupling reactions[24] of Compound 13 with (2-tributylstannyl)pyrazine or (5-tributylstannyl)pyrimidine proceeded to give 3β-hydroxy-17-(2-pyrazyl)-androsta-5,16-diene (14, 15%), and 3β-hydroxy-17-(5-pyrimidyl)-androsta-5,16-diene (15, 10%), respectively. The low yields of these two cross-coupling reactions may be due to instability of the stannyldiazine reagents under the reaction conditions employed. The structures of the target Compounds 14 and 15 were readily identified by their proton NMR spectra: The three nonequivalent protons of the 17-pyrazine moiety in Compound 14 appeared as three singlets at δ 8.35, 8.48 and 8.70, while for the three protons of the 17-pyrimidine moiety in Compound 15, two equivalent protons appear as a singlet at δ 8.73 and one proton appeared at δ 9.07. Furthermore, the 17-diazine groups of Compounds 14 and 15 exhibit different influences on the chemical shifts of their respective 16-olefinic protons with respect to the 16-proton of the precursor Δ$^{16}$-17-iodide 13: the 16-H in Compound 14 appeared as a singlet at δ 6.77, being significantly deshielded compared to the 16-H in Compound 13 (δ 6.14); the 16-H in Compound 15 appeared at δ 6.11, similar to Compound 13. During the course of this work we became aware that Compound 15 has been reported previously by Haidar et al.[20a] and its biological and pharmacological activities have also been described.[20b] However, it was synthesized by a procedure that is different from the one described herein.

In one embodiment, the prodrug of this invention includes a pharmaceutically acceptable prodrug group at the Y position of the compound of formula I. As used herein, "prodrug group" refers to a type of protecting or masking group that converts the drug into a prodrug. Prodrug groups are typically attached to the functional group of the drug via bonds that are cleavable under specified conditions of use. The benefit of the prodrug variants of the above compounds include improved oral pharmacokinetics and bioavailability. The present invention includes prodrug variants of any of the above compounds. However, for simplicity, the prodrugs of this invention will be described below with specific reference to Compound 5.

As discussed above with reference to the Y-group of compound formula I, exemplary suitable prodrug groups include amino acid groups, succinate groups, phosphate groups, or sulfamate groups.

Suitable amino acid prodrug groups include an amino acid selected from alanine, arginine, aspartic acid, glutamic acid, histidine, isoleucine, leucine, proline, serine, tyrosine, glycine, aspartic acid, valine, lysine, phenylalanine and combinations thereof. The amino acid prodrug group attaches to the 3-carbon on the A ring of Compound 5 by an ester linkage. Desirably, all the amino acids used as prodrug groups will be of L-form, as this form will be easily cleaved in vivo. The following compounds represent exemplary amino acid based prodrugs of Compound 5:

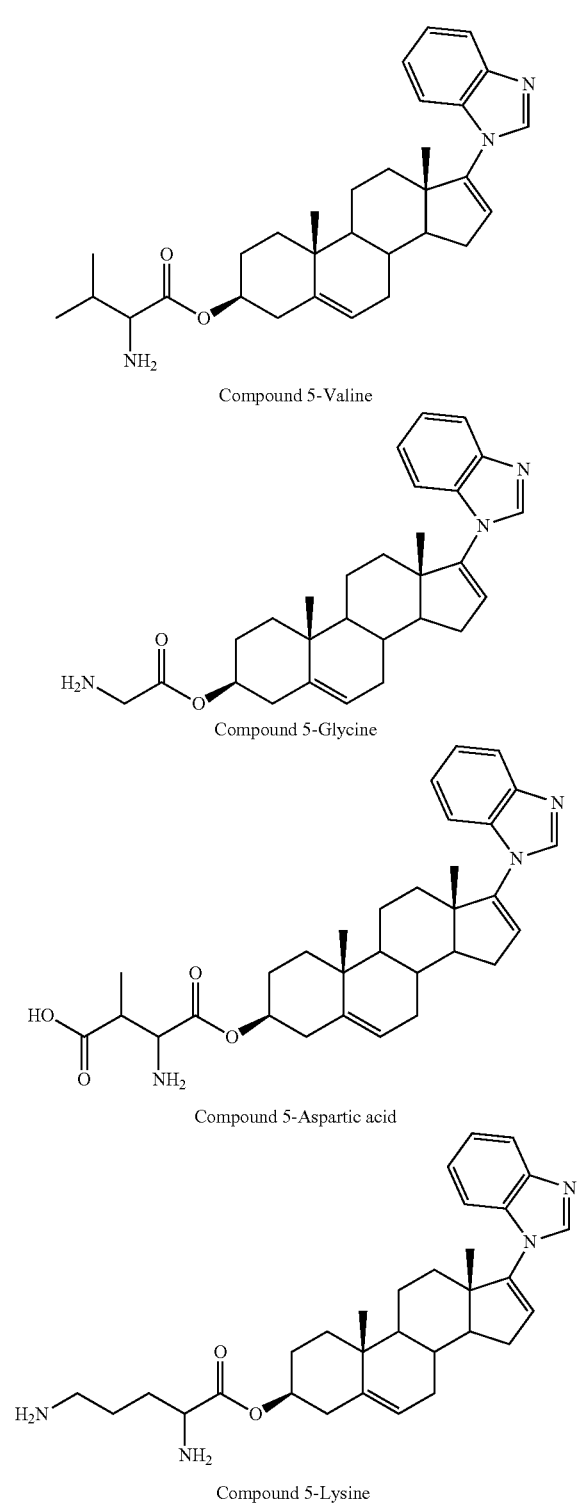

Compound 5-Valine

Compound 5-Glycine

Compound 5-Aspartic acid

Compound 5-Lysine

In one embodiment of this invention, the amino acid ester prodrug groups include dipeptide prodrugs using the following amino acids: alanine, arginine, aspartic acid, glutamic acid, histidine, isoleucine, leucine, proline, serine, tyrosine, glycine, aspartic acid, valine, lysine and phenylalanine Again, the preferred form of these amino acids will be L-form. The dipeptide can include two different amino acids, or be a dipeptide derived from same amino acid.

The synthesis of the above prodrugs Compound 5-Glycine, Compound 5-Valine and exemplary dipeptide ester prodrugs of Compound 5 are shown in Schemes 3-5. In an exemplary preparation of the prodrug Compound 5-Glycine according to Scheme 3, Boc-Glycine (1.2 mmol), is dissolved in DMF (5 ml). To this solution, Compound 5 (1 mmol), DMAP (1.2 mmol) and DCC (1.2 mmol) are added, sequentially. The reaction mixture is stirred at room temperature for 18 hours. The reaction mixture is added to water (50 ml) and the resulting precipitate will be filtered and dried. Flash column chromatography is used to purify the crude product. The pure product is further dissolved in DCM (10 ml) and cooled to 0° C. To this reaction mixture, dry HCl is bubbled (HCl will be generated from NaCl and $H_2SO_4$) for 30 minutes. The reaction mixture will be allowed to attain room temperature is further be stirred for 1 hour. Upon completion of the reaction, the reaction mixture is neutralized with sodium bicarbonate solution. The resulting prodrug Compound 5-Glycine is recrystallized in $CH_2Cl_2$/MeOH.

As shown in Scheme 3, the dipeptide prodrug Compound 5-Glycine-Glycine is obtained by repeating the above steps using the prodrug Compound 5-Glycine as the starting material and using HOBt instead of DMAP in the coupling reaction. The prodrug Compound 5-Valine, as shown in Scheme 4, is synthesized in the same manner described above for Compound 5-Glycine in Scheme 3, except that Boc-Valine is used instead of Boc-Glycine. Scheme 5 demonstrates forming and using the prodrug Compound 5-Glycine as a starting material to form, in a manner similar to Scheme 3, the Compound 5-Glycine-Valine dipeptide prodrug of this invention.

An exemplary method of obtaining the prodrug Compound 5-Lysine is shown in Scheme 6, and includes coupling an N-hydroxysuccinamide ester of Boc-protected L-lysine (1.2 mmol) with Compound 5 (1 mmol) in THF/Water using sodium bicarbonate (1.2 mmol) as base. The Boc-group is de-protected using dry HCl in dichloromethane at room temperature. The HCl salt is then filtered and dried. A neutralization of the HCl salt with aqueous sodium bicarbonate provides the Compound 5-Lysine.

An exemplary method of obtaining the prodrug Compound 5-Aspartic acid is shown in Scheme 7, and includes coupling of Boc-L-Aspartic acid benzyl ester with Compound 5 using DCC/DMAP in DMF to provide the ester derivative. Deprotection of the Boc group using a similar method as described above with the Compound 5-Glycine will give a benzyl ester derivative. The benzyl group is removed by treatment with palladium charcoal in the presence of formic acid in methanol to provide the prodrug Compound 5-Aspartic acid.

Succinate prodrug groups and phosphate prodrug groups are also connected to the A ring by an ester linkage. Succinate and phosphate prodrugs of Compound 5 are shown in Schemes 8 and 9, respectively. In the exemplary preparation of the prodrug Compound 5-Succinate according to Scheme 8, Compound 5 is refluxed in pyridine with succinic anhydride to provide the prodrug Compound 5-Succinate of this invention. In the exemplary preparation of the prodrug Compound 5-Phosphate according to Scheme 9, Compound 5 is dissolved in a dichloromethane/acetonitrile (1:1) mixture. To the dissolved Compound 5, ditert-butyl diisopropyl phosphorimidite and 1H-tetrazole are added. The reaction mixture is further treated with tert-butyl hydroperoxide at room temperature. The resulting intermediate compound is reacted with 2M HCl in THF at room temperature to yield the prodrug Compound 5-Phosphate of this invention.

A preferred sulfamate prodrug of Compound 5 is shown below.

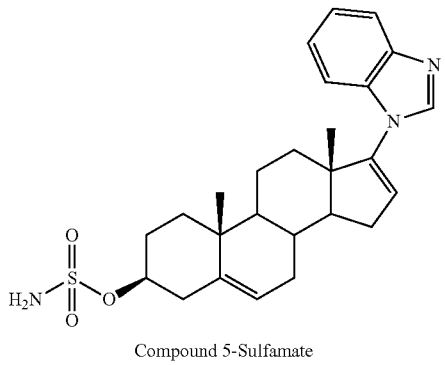 [SMILES: C[C@]12CC[C@H](OS(N)(=O)=O)CC1=CCC1C2CC[C@]2(C)C(n3cnc4ccccc43)=CCC12]

Compound 5-Sulfamate

In an exemplary preparation of the above prodrug Compound 5-Sulfamate according to Scheme 10, a stirring ice cold solution of Compound 5 (388 mg, 1 mmol) in DMF (5 ml) at 0° C. is treated with potassium tert-butoxide solution (1.2 ml, 1.2 mmol, 1M in THF) and is maintained at 0° C. for 0.5 hours. Sulfamoyl chloride (5 ml, 5 mmol, 1M in toluene) is added dropwise over 0.5 hours (sulfamoyl chloride can be prepared by an adaptation of the method of Appel, R.; Berger, G. Uber das hydrazidosufamid (On hydrazidosulfamide), Chem. Ber. 1958, 91, 1339-1341). The reaction mixture is allowed to attain room temperature over 2 hours, is then re-cooled to 0° C., and is then quenched by addition of first saturated solution of ammonium chloride (5 ml) and then diluted water (30 ml). Following an extraction with ethyl acetate (3×25 ml), the organic layers are washed with brine (3×25 ml), dried over anhydrous odium sulfate and then evaporated to give pure Compound 5-Sulfamate as white solid (mp=159-160° C.; $^1H$ NMR δ 0.99 (s, 3H, C-19 Hs), 1.033 (s, 3H, C-18 Hs), 4.25 (p, 1H, C-3H), 5.44 (s, 1H, C-6H), 5.74 (s, 1H, $C_{-16}$), 7.15 (s, 1H, Ar), 7.25 (s, 1H, Ar), 7.45 (s, 1H, Ar), 7.71 (s, 1H, Ar), 8.31 (s, 1H, Ar). HRMS $C_{26}H_{33}N_3O_3SNa^+$ found 490.212439, calcd 490.213484).

The present invention also provides a pharmaceutical composition comprising a pharmaceutically acceptable carrier and one or more of the prodrugs of this invention discussed above. Suitable pharmaceutically acceptable carriers described herein, for example, vehicles, adjuvants, excipients, and diluents, are well-known to those skilled in the art and are readily available to the public. The choice of carrier will be determined, in part, by the particular composition and by the particular method used to administer the composition. Accordingly, there are a wide variety of suitable formulations of the pharmaceutical compositions of the present invention.

The present invention also relates to method of treating diseases or conditions, such as cancer or other urogenital diseases and conditions, including, without limitation, breast cancer, prostate cancer, other urogenital cancers, prostate hyperplasia, or other androgen-related diseases or conditions, by administering to a subject in need thereof an effective amount of a prodrug compound in accordance with the present invention. The term "treating" is used conventionally, e.g., the management or care of a subject for the purpose of combating, alleviating, reducing, relieving, improving, etc., one or more of the symptoms associated with the prostate disease. Examples of prostate diseases that can be treated include, e.g., prostatic hyperplasia (BPH), and prostate cancer (e.g., prostatic adenocarcinoma). The treatment can be prophylactic or therapeutic. "Prophylactic" refers to any degree in inhibition of the onset of a cellular disorder, including complete inhibition, such as in a patient expected to soon exhibit the cellular disorder. "Therapeutic" refers to any degree in inhibition or any degree of beneficial effects on the disorder in the mammal (e.g., human), e.g., inhibition of the growth or metastasis of a tumor.

One skilled in the art will appreciate that suitable methods of administering a prodrug of the present invention to an animal, e.g., a mammal such as a human, are known. Although more than one route can be used to administer a particular composition, a particular route can provide a more immediate and more effective result than another route.

Formulations suitable for oral administration can consist of (a) liquid solutions, such as an effective amount of one or more prodrugs of this invention dissolved in a diluent, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically acceptable and compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The prodrugs of this invention, alone or in combination with other suitable components, can be made into aerosol formulations to be administered via inhalation. These aerosol formulations can be placed into pressurized acceptable propellants, such as dichlorodifluoromethane, hydrofluorocarbon (such as HFC 134a and/or 227), nitrogen, and the like.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to affect a therapeutic response in the animal over a reasonable time frame. The specific dose level and frequency of dosage may vary, depending upon a variety of factors, including the activity of the specific active compound, its metabolic stability and length of action, rate of excretion, mode and time of administration, the age, body weight, health condition, gender, diet, etc., of the subject, and the severity of, for example, the prostate cancer or hyperplasia. Any effective amount of the compound can be administered, e.g., from about 1 mg to about 500 mg per day, about 50 mg to about 150 mg per day, etc. In one embodiment of this invention, a suitable dosage for internal administration is 0.01 to 100 mg/kg of body weight per day, such as 0.01 to 35 mg/kg of body weight per day or 0.05 to 5 mg/kg of body weight per day. A suitable concentration of the compound in pharmaceutical compositions for topical administration is 0.05 to 15% (by weight), preferably 0.02 to 5%, and more preferably 0.1 to 3%. The prodrugs of this invention can be administered in such dosages in any form by any effective route, including, e.g., oral, parenteral, enteral, intraperitoneal, topical, transdermal (e.g., using any standard patch), ophthalmic, nasally, local, non-oral, such as aerosal, spray, inhalation, subcutaneous, intravenous, intramuscular, buccal, sublingual, rectal, vaginal, intra-arterial, and intrathecal, etc.

As discussed above, the prodrug of the present invention can be administered alone, or in combination with any ingredient(s), active or inactive, such as with a pharmaceutically acceptable excipient, carrier or diluent. The prodrugs of this invention can also be used in combination with other cancer treatments and drugs. For example, the prodrugs of this invention can be used as a part of or in combination with known cancer treatments such as hormone therapy, chemotherapy, radiation therapy, immunotherapy, and/or surgery. In one embodiment of this invention, one or more of the prodrugs described above is/are used in combination with one or more known and available drugs or other compounds. Exemplary drugs and/or hormones for use in combination with the prodrugs of this invention for treating cancer or other conditions or diseases discussed above include, without limitation, anti-androgonens such as flutamide and nilutamide; a CYP17 inhibitor such as abiraterone; luteinizing hormone-releasing hormone agonists such as leuprolide, goserelin and buserelin; drugs that prevent the adrenal glands from making androgens such as ketoconazole and aminoglutethimide; and estrogens. Other suitable and exemplary cancer drugs, common for use in chemotherapy, include, without limitation, cyclophosphamide, methotrexate, 5-Fluorouracil (5-FU), doxorubicin, carboplatin, carmustine, chlorambucil, cisplatin, cyclophosphamide, dacarbazine, ifosfamide, mechlorethamin, melphalan, procarbazine, bleomycin, doxorubicin, idarubicin mitoxantrone, chlorodeoxyadenosine, cytarabine, fludarabine, 6-mercaptopurine, methotrexate, 6-thioguanine, pentostatin, etoposide, gemcitabine, steroid creams, coritcosteroids, prednisone, and dexamethasone.

The prodrugs of this invention can be administered to a patient at any time as determined by the treating physician. Preferably, the prodrugs of this invention are administered for treating a patient during one or more of Stages II-IV of the cancer.

The data provided in WO 2006/093993, hereby incorporated by reference, reinforced the concept of modification of the C17 substituent of $\Delta^{16}$ steroids to produce potent inhibitors of CYP17 as well as potent AR antagonists. The data showed, for example, that the 17-benzimidazoles of Compounds 5 and 6 coordinate the heme iron of CYP17, a property that may in part be responsible for their enzyme inhibitory activity. Compounds 5 and 6 exhibited almost equipotent in vitro activities for CYP17 inhibition, AR antagonism, and inhibition of prostate cancer cell growth. The compounds were different in their antitumor activities, as Compound 5 caused marked suppression of LAPC4 tumor xenograft growth, and in contrast, Compound 6 (0.15 mmol/kg twice daily) enhanced tumor growth. The previous studies provided compelling evidence that Compound 5 is a potent inhibitor of human prostate tumor growth and is remarkably more effective than castration. This was the first example of a CYP17 inhibitor/antiandrogen demonstrating in vivo antitumor activity against a prostate cancer tumor to an extent that is superbly more effective than castration. These impressive biological activities, made Compound 5 a strong candidate for further development, such as according to the disclosure herein, as a potential drug for the treatment of prostate cancer in humans.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples. It is to be understood that any discussion of theory is included to assist in the understanding of the subject invention and is in no way limiting the invention in its broad application.

EXAMPLES

The effect of Compound 5 on the growth of the androgen-independent cell lines PC-3 and DU-145 was examined and it was found that Compound 5 inhibits their growth in a dose dependent manner in-vitro ($GI_{50}$=7.82 µM and 7.55 µM, respectively). The mechanism of action of Compound 5 in PC-3 cells was explored through microarray analysis and it was found that Compound 5 up-regulated genes involved in stress response and protein metabolism as well as down-regulated genes involved in cell cycle progression. Follow-up real-time PCR and western blot analyses revealed Compound 5 induces the endoplasmic reticulum stress response (ERSR) resulting in down-regulation of cyclin D1 protein expression and cyclin E2 mRNA. Cell cycle analysis confirmed G1/G0 phase arrest. Measurements of intracellular calcium levels ($[Ca^{2+}]_i$) demonstrated that 20 µM Compound 5 caused a release of $Ca^{2+}$ from ER stores resulting in a sustained rise in $[Ca^{2+}]_i$. Finally, co-treatment of PC-3 cells with 5, 10, and 20 µM Compound 5 with 10 nM thapsigargin revealed a synergistic relationship between the compounds in inhibiting PC-3 cell growth. Taken together, these findings demonstrate Compound 5 is endowed with multiple anti-cancer properties that may contribute to its utility as a prostate cancer therapeutic.

As discussed above, Compound 5 has shown excellent anticancer properties both in-vitro and in-vivo, and has been shown to inhibit the growth of LAPC4 tumor xenografts more effectively than castration[25]. Compound 5 and structurally related CYP17 inhibitors including abiraterone also inhibit the growth of the androgen independent cell lines PC-3 and DU-145, and identify the endoplasmic reticulum stress response (ERSR) as the compound's mechanism of growth inhibition. Importantly, these effects were seen at concentrations previously shown to be achievable in both plasma and within tumors in mouse PCA xenograft models[25].

A center of protein-folding, the endoplasmic reticulum (ER) is extremely sensitive to disruptions in homeostasis, including disruptions in calcium concentrations. Such stresses induce the ERSR, also called the unfolded protein response. The ERSR is an evolutionarily conserved pathway that seeks to relieve the build-up of unfolded proteins in the ER. To achieve this, the cell first up-regulates ER-resident molecular chaperones such as glucose-regulated protein 78 (gp78/BiP)[26-28], and reduces ER load through phosphorylation of the α subunit of the eukaryotic translation initiation factor 2 (eIF2α)[29,30]. Phosphorylation of eIF2α results in attenuation of translation of non-essential proteins, including growth related proteins such as cyclin D1[31-35]. Though the ERSR is a survival pathway, prolonged stimulation of the ERSR results in growth arrest and apoptosis via the up-regulation of apoptotic related proteins including the CCAAT/enhancer-binding protein homologous transcription factor (CHOP)[36]. As a result, the ERSR has been implicated in the anti-cancer activities of many synthetic and natural cancer therapeutics including clotrimazole, fatty acid synthase inhibitors, cox-2 inhibitors, $3^13^1$-diindolylmethane, and eicosapentaenoic acid[32,37-39].

Compound 5 induces the ERSR, resulting in the up-regulation of ERSR associated genes and the phosphorylation of eIF2α. This leads to the inhibition of Cyclin D1 translation resulting in G1 arrest. Analysis of intracellular calcium signaling reveals Compound 5 causes the release of $Ca^{2+}$ from the ER resulting in the depletion of ER calcium stores, and a sustained rise in intracellular $Ca^{2+}$ concentrations ($[Ca^{2+}]_i$).

Compound 5 (VN/124-1), Compound 6 (VN/125-1), Compound 16 (VN/63-1), Compound 17 (VN/85-1), and abiraterone were synthesized in our laboratory as previously described[22,25,41,42]. Thapsigargin, cyclopiazonic acid (CPA), and dihydroandrosterone (DHA) were purchased from Sigma Aldrich (St Louis, Mo., USA). Compounds were dissolved in either 95% ethanol or dimethyl sulfoxide. For all experiments, control cells were dosed with equal volume of vehicle (0.1% or less) as used in the treated groups.

Cell Culture and Viability Assays:

All cell lines were obtained from American Type Culture Collection (Rockville, Md.) and maintained in RPMI 1640 media supplemented with 10% fetal bovine serum and 5% penicillin/streptomycin solution. Cells were grown as a monolayer in a humidified incubator (5% $CO_2$) at 37° C. To determine the effect of the compounds on cell proliferation, cells were plated (2500 cells/well) in 96-well cell culture dishes (Corning, Inc. Corning, N.Y.). After a 24 hr attachment period, media was replaced with fresh media containing compounds (0.01 µM-100 µM) or vehicle (95% ethanol). The cells were then allowed to grow in the presence of the drugs for 96 hours. After 96 hours, relative cell viability was assessed using the MTT reagent (3-(4,5-dimethylthiazol-2-yl)-2,5-diphenyltetrazolium bromide) as described in Patel, et al. 2004[43]. Experiments were carried out three times with six replicates per dose per experiment (n=18). Results were plotted using the average of each dose over all three experiments and fitted with a best-fit sigmoidal dose response variable slope curve using GraphPad Prism 4.01 (GraphPad Software, Inc.). For combination of Compound 5 and Thapsigargin, cells were treated for 72 hrs and viability was assessed as described for single agents. Combination index (CI) was calculated as previously described[44]. CI values less than 1 are considered synergistic.

Microarray:

PC-3 cells were treated with (95% ethanol) or 20 µM of Compound 5. After 24 hour exposure to the agent, total RNA was isolated using the Qiagen RNeasy-Mini Kit following the manufacturer's protocol. Experiments were carried out in duplicate, with triplicate samples (dosed independently on 3 different days) from each experiment pooled for analysis on a single chip. Samples were hybridized to a GeneChip® Human Genome Focus Array (Affymetrix Inc., U.S.A.) and analyzed using an Affymetrix Genechip Scanner 3000 according to the manufacturer's protocol. Gene ontologies were identified using the online Database for Annotation, Visualization, and Integrated Discovery (DAVID) provided by the National Institute of Allergy and Infectious Diseases and the National Institute of Health. Only genes that were up or down-regulated by an average of ≥2-fold and had a minimum 1.5-fold change (up or down) per array were used for this analysis. Genes that showed ≥1.5-fold change (up or down) in control samples on one or both chips were excluded. Stringent criteria of a minimum EASE/P-Value threshold of 0.001 and a gene count threshold of 5 were used to identify altered gene ontologies.

Real-Time PCR:

Cells were treated, lysed and RNA collected and quantified using the same method outlined above. Cells were dosed independently on three separate days (n=3). 1 µg of total RNA was converted to cDNA using ReactionReady™ First Strand cDNA Synthesis kit (SuperArray Bioscience Corp.; Frederick, Md.) following the manufacturer's protocol. 50 ng of template cDNA was then used in subsequent real-time PCR (qRT-PCR) reactions. Template was combined with target gene specific or β-actin control $RT^2$ PCR Primer Sets, $RT^2$ Real-Time™ SYBR Green/Rox Master Mix (SuperArray Bioscience Corp.), and $ddH_2O$ for a final reaction volume of 25 µL and run on a 7900HT Fast Real-Time PCR system (Applied Biosystems; Foster City, Calif.) following the manufacturer's protocol. Fold changes were calculated using the $\Delta\Delta C_t$ method as recommended by the manufacture's protocol.

Cell Cycle Analysis

Cells were synchronized in the G1/G0 phase by maintaining them in 0.2% FBS-containing media for 96 hours. After starvation, media was replaced with normal growth media (10% FBS) containing vehicle (95% ethanol) or 20 µM VN/124-1 for 12, 18, and 24 hours. At each timepoint, cells were fixed in 70% ethanol at −20° C. for at least 24 hours. Fixed cells were then incubated with 1 mL propidium iodide (PI) staining buffer (1 mg/ml PI, 0.1% Triton-X, and 10 µh/ml RNase A dissolved in PBS) for 1 hour at room temperature and DNA content was measured by flow cytometry analysis using a FACSort flow cytometer (Becton Dickinson, San Jose, Calif.); 15,000 events were analyzed for each sample. ModFit LT version 3.1 (Verity Software House Ind., ME) was used to analyze cell cycle distribution.

Western Blot

Cells were treated with Compound 5, DHA, thapsigargin or vehicle for 6 and 24 hours. Protein was isolated, subjected to SDS-PAGE, transferred and imaged as previously described[45]. All primary antibodies were purchased from Cell Signaling (Danvers, Mass.). Quantitation of relative protein expression was determined via densitometry using the software ImageQuant 5.0 (Molecular Dynamics) with each protein normalized to its respective loading control. Results represent the average of at least three independent experiments, with representative blots shown.

$Ca^{2+}$ Measurements

PC-3 Cells were loaded with either fura-2 or fluo-3 indicator by incubation with 2 µM fura-2/AM or 2 µM fluo-3/AM in RPMI 1640 medium containing 10% fetal bovine serum for >60 min at room temperature. During experiments, the coverslips were mounted in a flow chamber and superfused with oxygenated Locke solution containing (in mM): 10 glucose, 136 NaCl, 5.6 KCl, 1.2 $NaH_2PO_4$, 14.3 $NaHCO_3$, 1.2 $MgCl_2$, and 2.2 $CaCl_2$, pH 7.4, at room temperature (22-24° C.).

For measurement of $[Ca^{2+}]$ in individual cells, PC-3 cells were treated with 1, 5, 10 and 20 µM Compound 5, 20 µM DHA, or vehicle. Cells loaded with fura-2 were placed in a perfusion chamber mounted on an inverted microscope (TE200; Nikon, Tokyo, Japan) equipped with a UV-transmitting objective (SuperFluor, 40×, N.A. 1.4, Nikon). Fura-2 was alternately excited by 340 nm and 380 nm light from monochromaters (Deltascan Illumination System, Photonic Technology International (PTI), South Brunswick, N.J.) and fura-2 emission was passed through a 515 nm longpass filter before detection by a cooled CCD camera (Retiga 2000R, Q-Imaging, Burnaby, Canada). For measurement of $Ca^{2+}$ transients in individual cells, coverslips with fluo-3 loaded cells were excited by the output of a 100 W mercury arc lamp that passed through a 480 nm bandpass filter (30 nm bandwidth). Fluorescence emission was passed through a 515 nm longpass filter before capture by a cooled CCD camera (Retiga 2000R, Q-Imaging). Image acquisition was performed with QCapture Pro (Q-Imaging) and analysis was performed with ImageJ (U.S. National Institutes of Health, Bethesda, Md., USA).

Fluo-3 $Ca^{2+}$ indicator measurements are reported as the fractional change in fluorescence intensity relative to baseline ($\Delta F/F_0$), which was determined as follows. Within a temporal sequence of fluorescence images, a region of interest (ROI) was drawn around each cell to be analyzed. The fluorescence signal from each cell was calculated as the pixel-averaged intensity within each ROI. In these experiments, a slight downward drift in baseline was typically observed, which was principally attributable to photo-bleaching of the indicator. In such cases, the drift was always well fit by a low-amplitude single-exponential decay. The fitted baseline value ($F_0$) at every time point was then used to calculate $\Delta F/F_0$. $\Delta F/F_0$ values are reported as mean±SE. For fura-2 measurements, $[Ca^{2+}]_i$ was derived using the ratio method of Grynkiewicz et al.[46]

Statistical Analysis qRT-PCR results for each gene were analyzed via a T-test comparing $\Delta Ct$ values (Ct value of test gene minus β-actin control). Western blots and combination growth studies were analyzed with a Kruskal-Wallis and Dunn's multiple comparison post-hoc. Flow cytometry data was analyzed with a T-test. $[Ca^{2+}]_i$ data was analyzed with a one-way ANOVA with a Dunnett's post-hoc.

Results

Figure 1B:
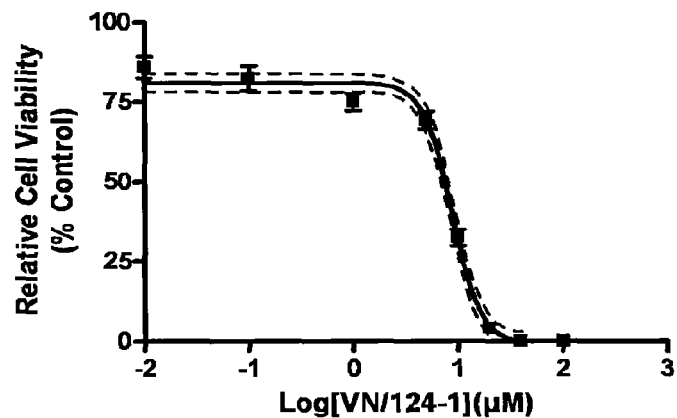
Figure 1C:
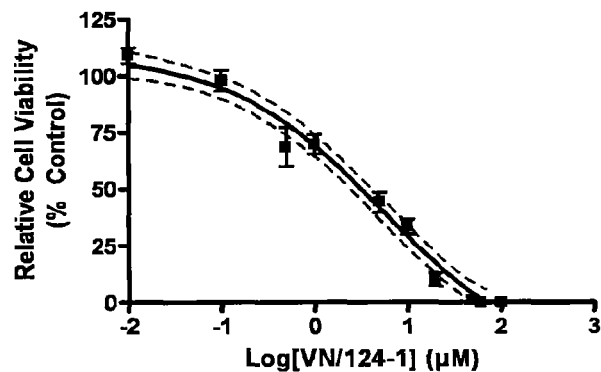

Compound 5 and Related C-17 Steroidal Azolyl Compounds Inhibit the Growth of AI PCA Cell Lines To determine if Compound 5 exerts a direct cytotoxic/cytostatic effect, the androgen independent prostate cancer cell lines PC-3 and DU-145 were treated with increasing concentrations of Compound 5 and it was found that the compound inhibited both cell lines in the low micromolar range (FIGS. 1A-C; Table 2). The potency of Compound 5 against PC-3 and DU-145 cell lines was comparable to that seen with androgen dependent LNCaP cells (low micromolar range). Structurally related steroidal C-17 substituted lyase inhibitors Compound 16, Compound 17, Compound 6, and abiraterone, also inhibited the growth of PC-3 and DU-145 cells (Table 2). The structurally related androgen, dihydroandrosterone (DHA), however, was almost a 10-fold less potent than Compound 5 in inhibiting PC-3 cells, and lacked any growth inhibitory activity against DU-145 cells up to 100 µM Inhibition of LNCaP cell viability in-vitro was previously attributed to the ability of Compound 5 to act as an AR antagonist. However, as PC-3 and DU-145 cells are well established androgen independent cell lines that do not express a functional AR[47], it is clear from these results that these compounds also have activity distinct from the androgen axis.

TABLE 2

| Compound | Cell Line | $GI_{50}$ (µM) | 95% C.I. (µM) | $GI_{90}$ (µM) | 95% C.I. (µM) |
|---|---|---|---|---|---|
| VN/63-1 | PC-3 | 2.91 | 1.14-11.57 | >100 | — |
| VN/85-1 | | 1.86 | 1.31-2.86 | 30.41 | 13.18-67.61 |
| VN/124-1 | | 7.82 | 7.13-8.38 | 18.62 | 16.10-21.88 |
| VN/125-1 | | 1.41 | 1.22-1.60 | 8.07 | 6.61-9.80 |
| Abiraterone | | 9.32 | 8.69-9.94 | >100 | — |
| DHEA | | 67.6 | 58.8-74.1 | >100 | — |
| VN/63-1 | DU-145 | 11.04 | 4.75-22.74 | >100 | — |
| VN/85-1 | | 5.31 | 3.71-7.22 | 31.62 | 23.12-40.58 |

TABLE 2-continued

| Compound | Cell Line | GI$_{50}$ (μM) | 95% C.I. (μM) | GI$_{90}$ (μM) | 95% C.I. (μM) |
|---|---|---|---|---|---|
| VN/124-1 | | 7.55 | 6.90-8.11 | 15.95 | 13.86-18.24 |
| VN/125-1 | | 6.57 | 5.58-7.51 | 15.53 | 12.40-19.55 |
| Abiraterone | | 14.68 | 13.42-15.95 | >100 | — |
| DHEA | | >100 | — | — | — |
| VN/63-1 | LNCaP | 1.05 | 0.69-1.55 | >100 | — |
| VN/85-1 | | 2.47 | 1.55-3.96 | 36.49 | 23.03-58.74 |
| VN/124-1 | | 3.15 | 2.41-4.17 | 31.99 | 23.82-45.01 |
| VN/125-1 | | 1.18 | 0.95-1.48 | 13.46 | 9.80-18.01 |
| Abiraterone | | 1.41 | 0.95-1.96 | 25.12 | 14.19-100 |
| DHEA | | NT* | — | — | — |

*NT = not tested

Microarray Analysis Reveals Compound 5 Induces the Down-Regulation of Cell Cycle Related Genes and Up-Regulation of Genes Involved in Cellular Response to Stress in PC-3 Cells.

To shed light on the mechanism of action of Compound 5, PC-3 cells were treated with 20 μM (~GI$_{90}$) of the compound for 24 hrs and global gene expression changes were measured using a GeneChip® Human Genome Focus Array. The online database was used for annotation, visualization, and integrated discovery (DAVID) to identify clusters of related genes affected by Compound 5. As shown in Table 3 (top panel), the most enriched up-regulated ontologies are those relating to stress and metabolism, in particular amino acid metabolism. Nearly all of the down-regulated ontologies (Table 3, bottom panel) are associated with the cell cycle, especially S-phase (DNA replication). Interestingly, induction of genes involved in amino acid metabolism has been shown to occur following induction of ER stress[48], and the ERSR is known to block the transition to S-phase of the cell cycle. These preliminary findings lead us to hypothesize that Compound 5 may inhibit growth via induction of the ERSR.

TABLE 3

| | Count | % | P-Value |
|---|---|---|---|
| Up-regulated Ontology | | | |
| Response to Stress | 16 | 24.24 | 1.93E-05 |
| Amino Acid Metabolism | 8 | 12.12 | 6.97E-05 |
| Amine Metabolism | 9 | 13.64 | 1.01E-04 |
| Nitrogen Compound Metabolism | 9 | 13.64 | 1.61E-04 |
| Amino Acid and Derivative Metabolism | 8 | 12.12 | 1.77E-04 |
| Negative Regulation of Biological Process | 12 | 18.18 | 1.90E-04 |
| Negative Regulation of Cellular Process | 11 | 16.67 | 4.57E-04 |
| Development | 18 | 27.27 | 6.29E-04 |
| Carboxylic Acid Metabolism | 9 | 13.64 | 7.48E-04 |
| Organic Acid Metabolism | 9 | 13.64 | 7.68E-04 |
| Response to External Stimulus | 9 | 13.64 | 9.76E-04 |
| Down-Regulated Ontology | | | |
| DNA Replication | 17 | 34.69 | 3.82E-19 |
| DNA Metabolism | 19 | 38.78 | 2.98E-13 |
| DNA-Dependent DNA Replication | 10 | 20.41 | 6.88E-12 |
| Cell Cycle | 16 | 32.65 | 1.41E-09 |
| Biopolymer Metabolism | 27 | 55.1 | 1.51E-08 |
| Regulation of Progression Through Cell Cycle | 10 | 20.41 | 9.25E-06 |
| Regulation of Cell Cycle | 10 | 20.41 | 9.41E-06 |
| Nucleobase, Nucleoside, Nucleotide and Nucleic Acid Metabolism | 24 | 48.98 | 8.12E-05 |
| Macromolecule Metabolism | 28 | 57.14 | 9.94E-05 |
| Second-Messenger-Mediated Signaling | 6 | 12.24 | 2.86E-04 |

Compound 5 Induces Genes Involved in ER-Stress Response

Figure 2A:
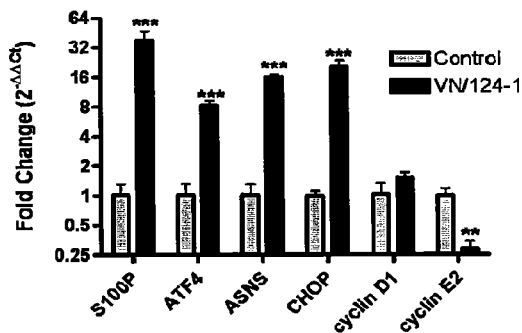
FIGS. 2A-C summarize inducement of the endoplasmic reticulum stress response (ERSR) through Compound 5, resulting in G1/G0 cell cycle arrest.

The gene expression changes of specific genes found to be altered by Compound 5 in the microarray experiment was validated by using quantitative real-time PCR (FIG. 2A). The most highly up-regulated gene found in the microarray was S100P calcium binding protein (S100P). S100P is a member of the S100 family of proteins, all of which take part in $Ca^{2+}$ signaling. Surprisingly, S100P has been shown to be involved in the growth and survival of cancer cells and is a negative prognostic marker of disease progression[49,50]. The functional significance of this remains unknown, but interestingly, S100P has been reported to be up-regulated by other chemotherapeutics and natural anticancer agents including DNA cross-linking agents and all-trans retinoic acid[51,52]. Other genes verified by qRT-PCR that were up-regulated in the microarray experiment include asparagines synthetase (ASNS) and activating transcription factor 4 (ATF4). Both of these genes have been reported to be up-regulated by the ERSR[38]. CHOP was not included in the microarray, but is a marker for the ERSR[36] and qRT-PCR revealed it to be strongly up-regulated by Compound 5. The expression of the G1 cyclins D1 and E2 was also looked at. Interestingly, cyclin D1 mRNA levels were not affected by Compound 5 but the downstream cyclin E2 was significantly reduced. These results were very similar to those seen in the microarray.

Compound 5 Induces ERSR Related Proteins, Phosphorylation of eIF2α, and Down-Regulation of Cyclin D1

Figure 2C:
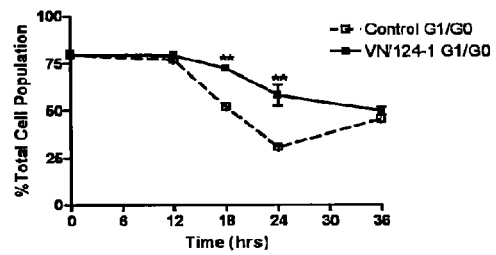
Figure 2B:
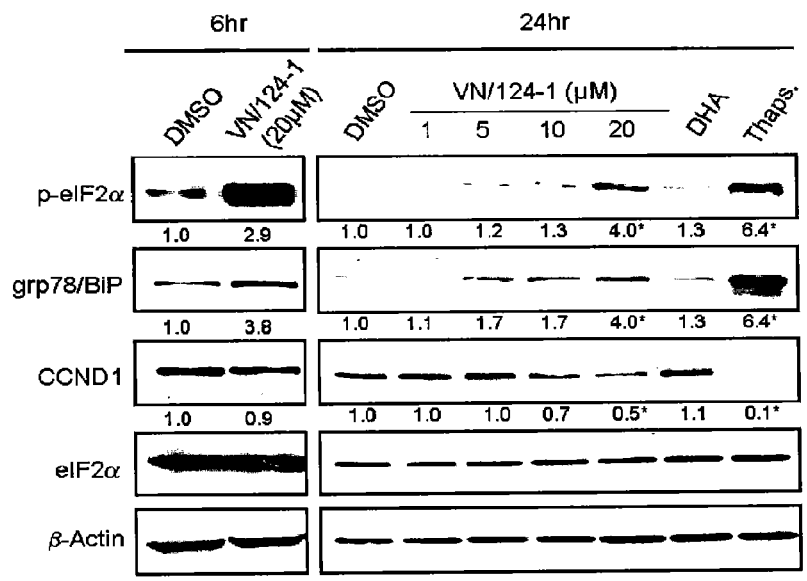

To confirm the ERSR as a mechanism of Compound 5 action, we next analyzed the effect of the drug at the protein level. PC-3 cells were treated with Compound 5 for 6 and 24 hours. As shown in FIG. 2B, 20 μM VN/124-1 induced the phosphorylation of eIF2α at 6 and 24 hours. The drug also significantly induced the expression of the molecular chaperone gp78/BiP, a well established marker of ER-stress[26-28], in a dose-dependent manner. As mentioned previously, phosphorylation of eIF2α attenuates translation of many transcripts including cyclin D1. This was confirmed as Compound 5 induced the down-regulation of cyclin D1 protein significantly after 24 hrs. As discussed above, Compound 5 had no effect on cyclin D1 mRNA levels, suggesting this down-regulation is indeed occurring at the translational level. Of note, treatment with 20 μM DHA had no significant effect on any of the protein markers measured. Taken together these findings strongly support the hypothesis that Compound 5 induces the ERSR.

Compound 5 Induces G1/G0 Growth Arrest

The effect of Compound 5 on cell cycle distribution in PC-3 cells was analyzed. The treatment with 20 μM Compound 5 was found to prevent the exit from G1 phase of the cell cycle in synchronized cells (FIG. 2C). This resulted in a significant increase in the amount of cells in G1/G0 at 18 and 24 hrs. These findings are in line with the loss of cyclin D1 protein expression and subsequently cyclin E2 transcription as both are needed for transition to the S-phase of the cell cycle[53]. This is also in accord with the microarray data showing Compound 5 down-regulates genes involved in DNA replication.

Compound 5 Induces Release of $Ca^{2+}$ from ER Stores

Figure 3A:
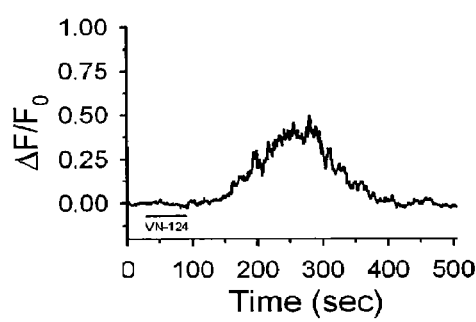
FIGS. 3A-D summarize Compound 5's induced release of calcium from the endoplasmic reticulum (ER). PC-3 cells loaded with Fluo-3AM were treated with 200 VN/124-1 in the presence (FIG. 3A) or absence (FIG. 3B) of extracellular calcium. Mean peak values are 0.613 and 0.967, respectively. For FIG. 3C, PC-3 cells were pretreated for 5 minutes with CPA prior to dosing with 200 Compound 5. For all treatments, $Ca^{2+}$ transients were measured in individual cells (n=9, 12, 9, respectively) as described in the Examples. For FIG. 3D, cells were dosed with increasing concentrations of Compound 5, 200 DHA or vehicle for 2 hrs and then loaded with Fura-2AM and absolute [Ca2+] were measured. Individual cells were counted (n=32) as described in the materials and methods. *p<0.05
Figure 3B:
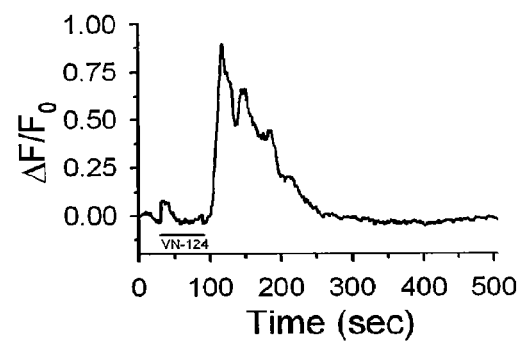
Figure 3C:
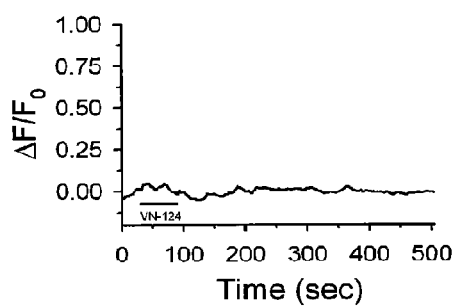
Figure 3D:
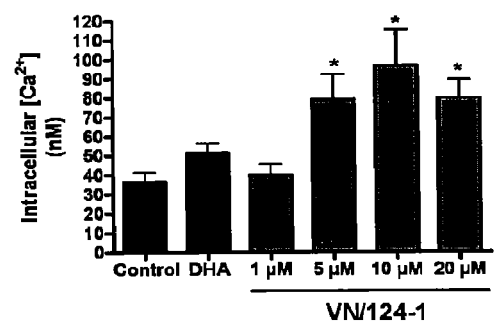

Some structurally related compounds including $3^13^1$-diindolylmethane and imidazole containing anti-fungals, such as clotrimazole and eiconazole, have been shown to elicit the ERSR by disrupting ER calcium homeostasis[32,54,55]. To determine if Compound 5 induces the ERSR in a similar manner, we treated PC-3 cells with 20 μM Compound 5 and measured relative changes in intracellular calcium concentrations $[Ca^{2+}]_i$ using the calcium sensitive fluorescent dye, Fluo-3AM. As seen in FIG. 3A, Compound 5 induced an immediate transient rise in $[Ca^{2+}]_i$ (mean $\Delta F/F_o$=0.613). This transient was not reduced when extracellular calcium was removed from the bath (mean $\Delta F/F_o$=0.967; FIG. 3B), but was completely abolished when ER calcium stores were depleted by pretreatment with the sarco/endoplasmic reticulum $Ca^{2+}$-ATPase (SERCA) inhibitor CPA (FIG. 3C). Finally, the sustained effect of Compound 5 was measured on absolute $[Ca^{2+}]_i$ using Fura-2AM. PC-3 cells were treated for 2 hours with vehicle, DHA, or increasing concentrations of Compound 5 (FIG. 3D). Control cells had an average $[Ca^{2+}]_i$ of 36.49 nM while cells treated with 5, 10 and 20 µM VN/124-1 had a significant increase in $[Ca^{2+}]_i$ (79.13, 96.63, and 79.89 nM, respectively). Treatment with DHA or 104 Compound 5 did not have a significant effect on $[Ca^{2+}]_i$. These results clearly demonstrate that Compound 5 is inducing $Ca^{2+}$ release from ER-stores, resulting in a sustained rise in $[Ca^{2+}]_i$.

Compound 5 Synergizes with Known ERSR Inducer Thapsigargin

Figure 4:
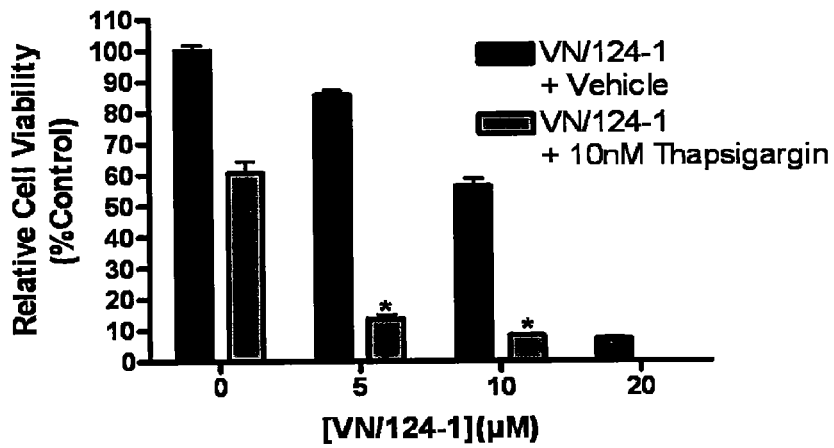
FIG. 4 summarizes the combination of Compound 5 and Thapsigargin. PC-3 cells were treated with 5, 10, or 20 µM Compound 5 plus 10 nM thapsigargin or vehicle (DMSO) for 96 hrs and cell viability was assessed via MTT assay. The combination was synergistic in inhibiting PC-3 cell growth at all three (CI=0.40, 0.58, 0.77, respectively). *p<0.01.

To determine if Compound 5 would act synergistically with a compound known to induce ER stress, PC-3 cells were co-treated with Compound 5 and the SERCA pump inhibitor thapsigargin. A sub-toxic dose of 10 nM thapsigargin was combined with 5, 10, and 2004 of Compound 5 and cell viability was measured after 96 hrs. As shown in FIG. 4, thapsigargin and Compound 5 act synergistically to inhibit the growth of PC-3 cells at all three concentrations (CI=0.40, 0.58, 0.77, respectively), further implicating the ERSR and calcium disruptions as Compound 5's mechanism of action.

Inhibitors of CYP17 are an exciting new class of potential prostate cancer therapeutics. As these drugs enter clinical trials, complete understanding of their mechanisms of action is important in evaluating their efficacy and safety. In the above Example it is demonstrated that the CYP17 inhibitor/anti-androgen Compound 5, as well as other structurally related CYP17 inhibitors, exerts direct growth inhibitory actions against the androgen independent cell lines PC-3 and DU-145. As these actions were seen in the low micromolar range, it is important to note that peak plasma concentrations of abiraterone (given clinically as the prodrug abiraterone acetate) are below 1 µM[56], suggesting these findings may not be relevant for that compound. However, pre-clinical kinetics data of Compound 5 has shown that concentrations above 20 µM are achievable in mouse in-vivo models[25], indicating these findings are physiologically relevant.

Figure 5:
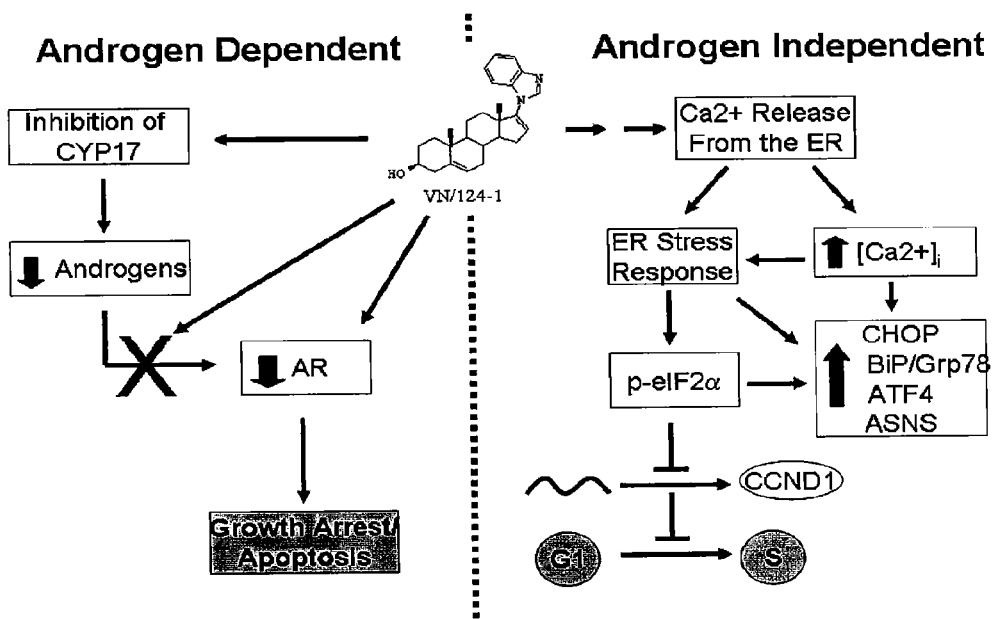
FIG. 5 representatively illustrates Compound 5's androgen-dependent and independent mechanisms of action.

Utilizing various molecular, pharmacological, and biochemical techniques the likely mechanism of Compound 5 action against androgen-independent PCA cells was identified (FIG. 5, right side). Compound 5 induces the rapid release of $Ca^{2+}$ from the ER, resulting in a sustained rise in $[Ca^{2+}]_i$. This disruption in $Ca^{2+}$ homeostasis induces the ERSR, resulting in the up-regulation of ERSR-related genes and the phosphorylation of eIF2α. Phosphorylation of eIF2α attenuates the translation of several pro-growth genes including cyclin D1. The loss of cyclin D1 prevents exit from the G1-phase of the cell cycle thereby inhibiting the growth of cells.

It remains unclear how Compound 5 induces release of $Ca^{2+}$ from the ER. Interestingly, the compound was shown to act synergistically with thapsigargin, suggesting Compound 5 works through a separate mechanism. Still, disruptions in $Ca^{2+}$ and induction of the ERSR are likely not to be selective for cancer cells in-vitro. However, there is a growing belief that agents that induce the ERSR may exhibit some specificity for tumors in-vivo as it is well documented that tumors are under constant low levels of ER stress[57]. This is in large part due to the hypoxic conditions of the tumor microenvironment. Recent studies with the ERSR-inducing compound, $3^13^1$-diindolylmethane (DIM), showed that cancer cells were sensitized to the drug when co-treated not only with thapsigargin, but also in media deficient in leucine and supplemented with 2-deoxyglucose and the Hifla inducer $CoCl_2$ to simulate the hypoxic and nutrient deficient environment of the tumor[38]. Therefore, it is possible that a therapeutic window exists where Compound 5 could be used to treat androgen-independent PCA without significant toxicity.

Compound 5 appears to be endowed with multiple pharmacological properties that add to its utility as a prostate cancer therapeutic. FIG. 5 outlines all of the androgen-dependent and independent mechanisms of Compound 5. Compound 5's major mechanism remains inhibition of CYP 17, which is achieved in the low nanomolar range. However, previous studies have shown high doses (0.15 mmol/kg b.i.d.) were capable of inhibiting tumors significantly better than castration in-vivo[25], suggesting Compound 5's ability to induce the ERSR may play a role at such doses. The findings outlined in this study represent a major step forward in the understanding of Compound 5's mechanism of action and underscore the drugs potential to be used to treat all phases of prostate cancer.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

REFERENCES

1. American Cancer Society—Cancer Facts and Figures 2008.
2. McConnell, J. D. Physiological basis of endocrine therapy for prostatic cancer. *Urol. Clin. North Am.,* 1991, 18: 1-13.
3. Bruchovsky, N.; Wilson, J. D. The conversion of testosterone to 5α-androstan-17β-ol-3-one by rat prostate in vivo and in vitro. *J. Biol. Chem.,* 1968, 243, 2012-2021.
4. Huggins, C.; Stephens, R. C.; Hudges, C. V. Studies on prostatic cancer: 2. The effects of castration on advanced carcinoma of the prostate gland. *Arch. Surg.,* 1941, 43, 209-212.
5. Denmeade, S. R.; Isaacs, J. T. A history of prostate cancer treatment. *Nature Rev. Cancer,* 2002, 2: 389-396.
6. Crawford, E. D.; Eisenberger, M. A.; McLeod, D. G.; Spaulding, J. T.; Benson, R.; Don, F. A.; Blumstein, B. A.; Davis, M. A.; Goodman, P. J. A controlled trial of leuprolide with and without flutamide in protatic carcinoma. *N Engl. J. Med.,* 1989, 321, 419-424.
7. Crawford, E. D.; Allen, J. A. Treatment of newly diagnosed state D2 prostate cancer with leuprolide and flutamide or leuprolide alone, Phase III: intergroup study 0036. *J. Urol.,* 1992, 147: 417A.
8. Denis, L. Role of maximal androgen blockade in advanced prostate cancer. *Prostate,* 1994, 5 (Suppl.), 17s-22s.
9. Mohler, J. L.; Gregory, C. W.; Harris Ford III, O.; Kim, D.; Weaver, C. M.; Petrusz, P.; Wilson, E. M.; French, F. S. The androgen axis in recurrent prostate cancer. *Clin. Cancer Res.,* 2004, 10, 440-448.
10. Chen, C. D.; Welsbie, D. S.; Tran, C.; Baek, S. H.; Chen, R.; Vessella, R.; Rosenfeld, G. M.; Sawyer, C. L. Molecular determinants of resistance to antiandrogen therapy. *Nat. Med.,* 2004, 10, 33-39.

11. Njar, V. C. O.; Brodie, A. M. H. Inhibitors of 17α-hydroxylase-$C_{17,20}$-lyase (CYP17): Potential agents for the treatment of prostate cancer. *Current Pharm. Design,* 1999, 5: 163-180.
12. Hall, P. F. Cytochrome P-450 $C_{21cc}$: one enzyme with two actions: Hydroxylase and lyase, *J. Steroid Biochem. Molec. Biol.,* 1991, 40, 527-532.
13. Trachtenberg, J.; Halpern, N.; Pont, A. Ketoconazole: A novel and rapid treatment for advanced prostatic cancer, *J. Urol.* 1983, 130, 152-153.
14. Muscato, J. J.; Ahmann, K. M.; Johnson, W.; Wilding, W.; Monaghan, G.; Schlossman, D. M. Optimal dosing of ketoconazole and hydrocrtisone leads to long responses in hormone refractory prostate cancer, *Proc. Am. Assoc. Cancer Res.,* 1994, 13: 22 (Abstract).
15. Small, E. J.; Baron, A. D.; Fippin, L.; Apodaca, D. Ketoconazole retains activity in advanced prostate cancer patients with progression despite flutamide withdrawal. *J. Urol.,* 1997, 157, 1204-1207.
16. O'Donnell, A.; Judson, I.; Dowsett, M.; Raynaud, F.; Dearnaley, D.; Mason, M.; Harland, S.; Robbins, A.; Halbert, G.; Nutley, B.; Jarman, M. Hormonal impact of the 17α-hydroxylase/C17,20-lyase inhibitors abiraterone acetate (CB7630) inpatients with prostate cancer. *Br. J. Cancer,* 2004, 90: 2317-2325.
17. Long, B. J.; Grigoryev, D. N.; Nnane, I. P.; Liu, Y.; Ling, Y-Z.; Brodie, A. M. Antiandrogenic effects of novel androgen synthesis inhibitors on hormone-dependent prostate cancer. *Cancer Res.,* 2000, 60, 6630-6640.
18. Lipinski, C. A., Drug-like properties and the causes of poor solubility and poor permeability. *J. Pharmacol Toxicol Methods* 2000, 44, (1), 235-49.
19. Veber, D. F.; Johnson, S. R.; Cheng, H. Y.; Smith, B. R.; Ward, K. W.; Kopple, K. D., Molecular properties that influence the oral bioavailability of drug candidates. *J Med Chem* 2002, 45, (12), 2615-23.
20. (a) Haidar, S.; Ehmer, P. B.; Hartmann, R. W. Novel steroidal pyrimidyl inhibitors of P450 17 (17α-hydroxylase/C17-20-lyase). *Arch. Pharm. Med. Chem.,* 2001, 334, 373-374. (b) Haidar, S.; Ehmer, P. B.; Barassin, S.; Batzl-Hartmann, C.; Hartmann, R. W. Effects of novel 17α-hydroxylase/C17,20-lyase (P45017, CYP17) inhibitors on androgen biosynthesis in vitro and in vivo. *J. Steroid Biochem. Molec. Biol.,* 2003, 84, 555-562.
21. Njar, V. C. O.; Klus, G. T.; Brodie, A. M. H. Nucleophilic vinylic "addition-elimination" substitution reaction of 3β-acetoaxy-17-chloro-16-formylandrosta-5,16-diene: A novel and general route to 17-substituted-$\Delta^{16}$-steroids. Part 1. Synthesis of novel 17-azolyl-$\Delta^{16}$ steroids; inhibitors of 17α-hydroxylase/17,20-lyase (P450$_{17α}$), *Bioorg. Med. Chem. Lett.,* 1996, 6, 2777-2782.
22. Njar, V. C. O.; Kato, K.; Nnane, I. P.; Grigoryev, D. N.; Long, B. J.; Brodie, A. M. H. Novel 17-azolyl steroids; potent inhibitors of cytochrome P450 17α-hydroxylase/17,20-lyase (P450$_{17α}$): Potential agents for the treatment of prostate cancer, *J. Med. Chem.,* 1998, 41, 902-912.
23. Potter, G. A.; Hardcastle, I. R.; Jarman, M. A convenient, large-scale synthesis of abiraterone acetate [3β-acetoxy-17(3-pyridyl)androsta-5,16-diene], a potential new drug for the treatment of prostate cancer. *Org. Prep. Proc. Int.,* 1997, 29, 123-128.
24. Choshi, T.; Yamada, S.; Sugino, E.; Kuwada, T.; Hibino, S. Total synthesis of Grossularines-1 and -2. *J. Org. Chem.,* 1995, 60, 5899-5904.
25. Handratta V D, Vasaitis T S, Njar V C, et al. Novel C-17-heteroaryl steroidal CYP17 inhibitors/antiandrogens: synthesis, in vitro biological activity, pharmacokinetics, and antitumor activity in the LAPC4 human prostate cancer xenograft model. *J Med Chem* 2005 48:2972-84.
26. Kaufman R J. Stress signaling from the lumen of the endoplasmic reticulum: coordination of gene transcriptional and translational controls. *Genes Dev* 1999 13:1211-33.
27. Mori K. Tripartite management of unfolded proteins in the endoplasmic reticulum. *Cell* 2000 101:451-4.
28. Liu H, Bowes R C, 3rd, van de Water B, Sillence C, Nagelkerke J F, Stevens J L. Endoplasmic reticulum chaperones GRP78 and calreticulin prevent oxidative stress, Ca2+ disturbances, and cell death in renal epithelial cells. *J Biol Chem* 1997 272:21751-9.
29. Harding H P, Zhang Y, Ron D. Protein translation and folding are coupled by an endoplasmic-reticulum-resident kinase. *Nature* 1999 397:271-4.
30. Shi Y, Vattem K M, Sood R, et al. Identification and characterization of pancreatic eukaryotic initiation factor 2 alpha-subunit kinase, PEK, involved in translational control. *Mol Cell Biol* 1998 18:7499-509.
31. Clemens M J. Targets and mechanisms for the regulation of translation in malignant transformation. *Oncogene* 2004 23:3180-8.
32. Aktas H, Fluckiger R, Acosta J A, Savage J M, Palakurthi S S, Halperin J A. Depletion of intracellular Ca2+ stores, phosphorylation of eIF2alpha, and sustained inhibition of translation initiation mediate the anticancer effects of clotrimazole. *Proc Natl Acad Sci USA* 1998 95:8280-5.
33. Lai E, Teodoro T, Volchuk A. Endoplasmic Reticulum Stress: Signaling the Unfolded Protein Response. *Physiology* 2007 22:193-201.
34. Prostko C R, Brostrom M A, Brostrom C O. Reversible phosphorylation of eukaryotic initiation factor 2 alpha in response to endoplasmic reticular signaling. *Mol Cell Biochem* 1993 127-128:255-65.
35. Ron D. Translational control in the endoplasmic reticulum stress response. *J Clin Invest* 2002 110:1383-8.
36. Zinszner H, Kuroda M, Wang X, et al. CHOP is implicated in programmed cell death in response to impaired function of the endoplasmic reticulum. *Genes Dev* 1998 12:982-95.
37. Palakurthi S S, Fluckiger R, Aktas H, et al Inhibition of translation initiation mediates the anticancer effect of the n-3 polyunsaturated fatty acid eicosapentaenoic acid. *Cancer Res* 2000 60:2919-25.
38. Sun S, Han J, Ralph W M, Jr., et al. Endoplasmic reticulum stress as a correlate of cytotoxicity in human tumor cells exposed to diindolylmethane in vitro. *Cell Stress Chaperones* 2004 9:76-87.
37. Little J L, Wheeler F B, Fels D R, Koumenis C, Kridel S J Inhibition of fatty acid synthase induces endoplasmic reticulum stress in tumor cells. *Cancer Res* 2007 67:1262-9.
40. Pyrko P, Kardosh A, Liu Y T, et al. Calcium-activated endoplasmic reticulum stress as a major component of tumor cell death induced by 2,5-dimethyl-celecoxib, a non-coxib analogue of celecoxib. *Mol Cancer Ther* 2007 6:1262-75.
41. Potter G A, Barrie S E, Jarman M, Rowlands M G. Novel steroidal inhibitors of human cytochrome P45017 alpha (17 alpha-hydroxylase-C17,20-lyase): potential agents for the treatment of prostatic cancer. *J Med Chem* 1995 38:2463-71.
42. Potter G A, Hardcastle I R, Jarman M. A Convenient, Large-Scale Synthesis of Abiraterone Acetate [β-Acetoxy-17-(3-pyridyl)androsta-5,16-dien], A Potential New Drug for the Treatment of Prostate Cancer. *Organic Preperations and Procedures Int* 1997 29:123-34.
43. Patel J B, Huynh C K, Handratta V D, et al. Novel retinoic acid metabolism blocking agents endowed with multiple biological activities are efficient growth inhibitors of human breast and prostate cancer cells in vitro and a human breast tumor xenograft in nude mice. *J Med Chem* 2004 47:6716-29.
44. Chou T C, Tan Q H, Sirotnak F M. Quantitation of the synergistic interaction of edatrexate and cisplatin in vitro. *Cancer Chemother Pharmacol* 1993 31:259-64.
45. Khandelwal A, Gediya L K, Njar V C. MS-275 synergistically enhances the growth inhibitory effects of RAMBA VN/66-1 in hormone-insensitive PC-3 prostate cancer cells and tumours. *Br J Cancer* 2008.
46. Grynkiewicz G, Poenie M, Tsien R Y. A new generation of Ca2+ indicators with greatly improved fluorescence properties. *J Biol Chem* 1985 260:3440-50.
47. Navone N M, Logothetis C J, von Eschenbach A C, Troncoso P. Model systems of prostate cancer: uses and limitations. *Cancer Metastasis Rev* 1998 17:361-71.
48. Lecca M R, Wagner U, Patrignani A, Berger E G, Hennet T. Genome-wide analysis of the unfolded protein response in fibroblasts from congenital disorders of glycosylation type-I patients. *FASEB J* 2005 19:240-2.
49. Arumugam T, Simeone D M, Schmidt A M, Logsdon C D. S100P stimulates cell proliferation and survival via receptor for activated glycation end products (RAGE). *J Biol Chem* 2004 279:5059-65.
50. Beer D G, Kardia S L, Huang C C, et al. Gene-expression profiles predict survival of patients with lung adenocarcinoma. *Nat Med* 2002 8:816-24.
51. Jiang F, Shults K, Flye L, et al. S100P is selectively upregulated in tumor cell lines challenged with DNA cross-linking agents. *Leuk Res* 2005 29:1181-90.
52. Shyu R Y, Huang S L, Jiang S Y. Retinoic acid increases expression of the calcium-binding protein S100P in human gastric cancer cells. *J Biomed Sci* 2003 10:313-9.
53. Lukas J, Herzinger T, Hansen K, et al. Cyclin E-induced S phase without activation of the pRb/E2F pathway. *Genes Dev* 1997 11:1479-92.
54. Savino J A, 3rd, Evans J F, Rabinowitz D, Auborn K J, Carter T H. Multiple, disparate roles for calcium signaling in apoptosis of human prostate and cervical cancer cells exposed to diindolylmethane. *Mol Cancer Ther* 2006 5:556-63.
55. Zhang Y, Soboloff J, Zhu Z, Berger S A. Inhibition of Ca2+ influx is required for mitochondrial reactive oxygen species-induced endoplasmic reticulum Ca2+ depletion and cell death in leukemia cells. *Mol Pharmacol* 2006 70:1424-34.
56. O'Donnell A, Judson I, Dowsett M, et al. Hormonal impact of the 17alpha-hydroxylase/C(17,20)-lyase inhibitor abiraterone acetate (CB7630) in patients with prostate cancer. Br J Cancer 2004 90:2317-25.
57. Moenner M, Pluquet O, Bouchecareilh M, Chevet E. Integrated endoplasmic reticulum stress responses in cancer. Cancer Res 2007 67:10631-4.

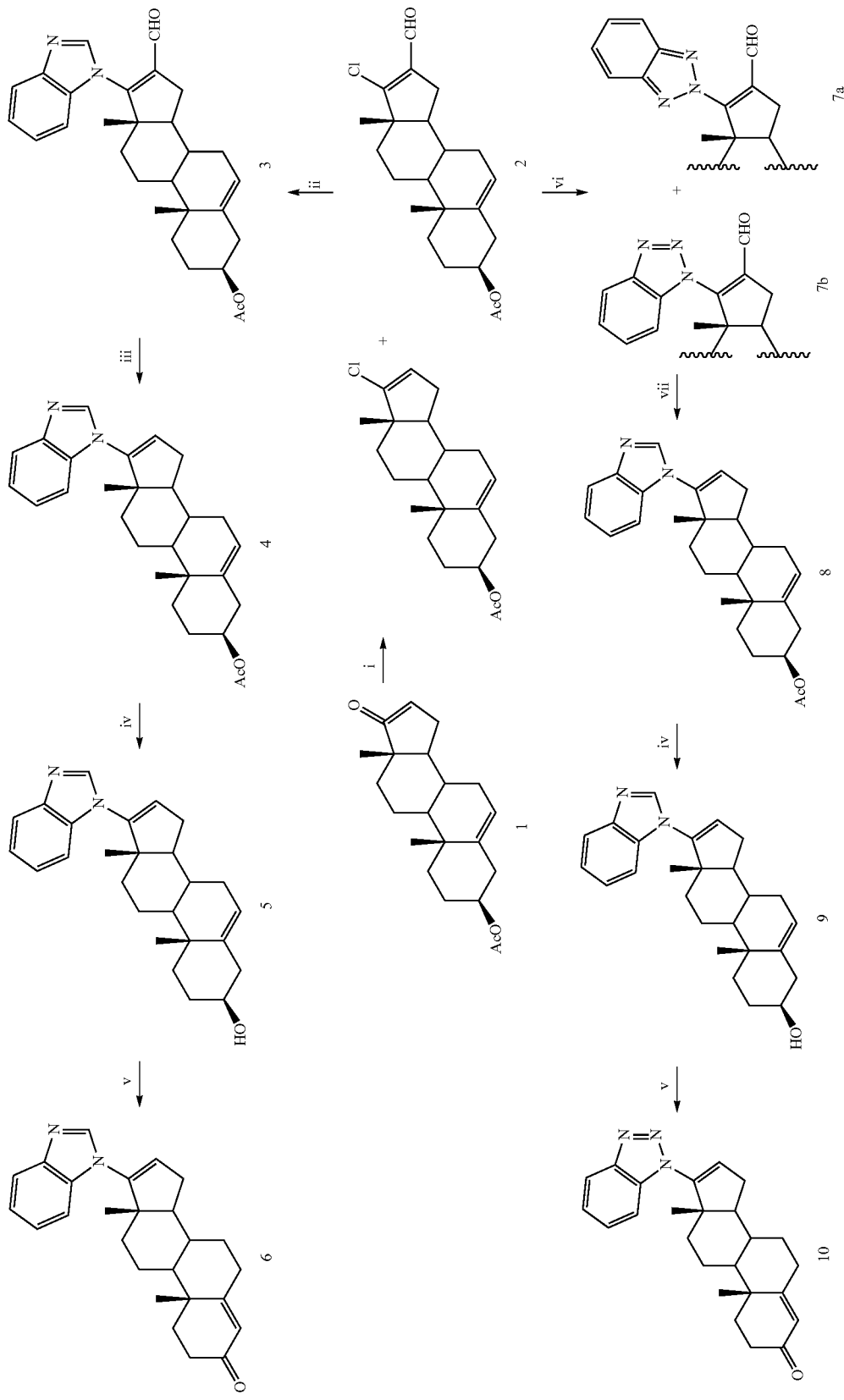

Scheme 2:
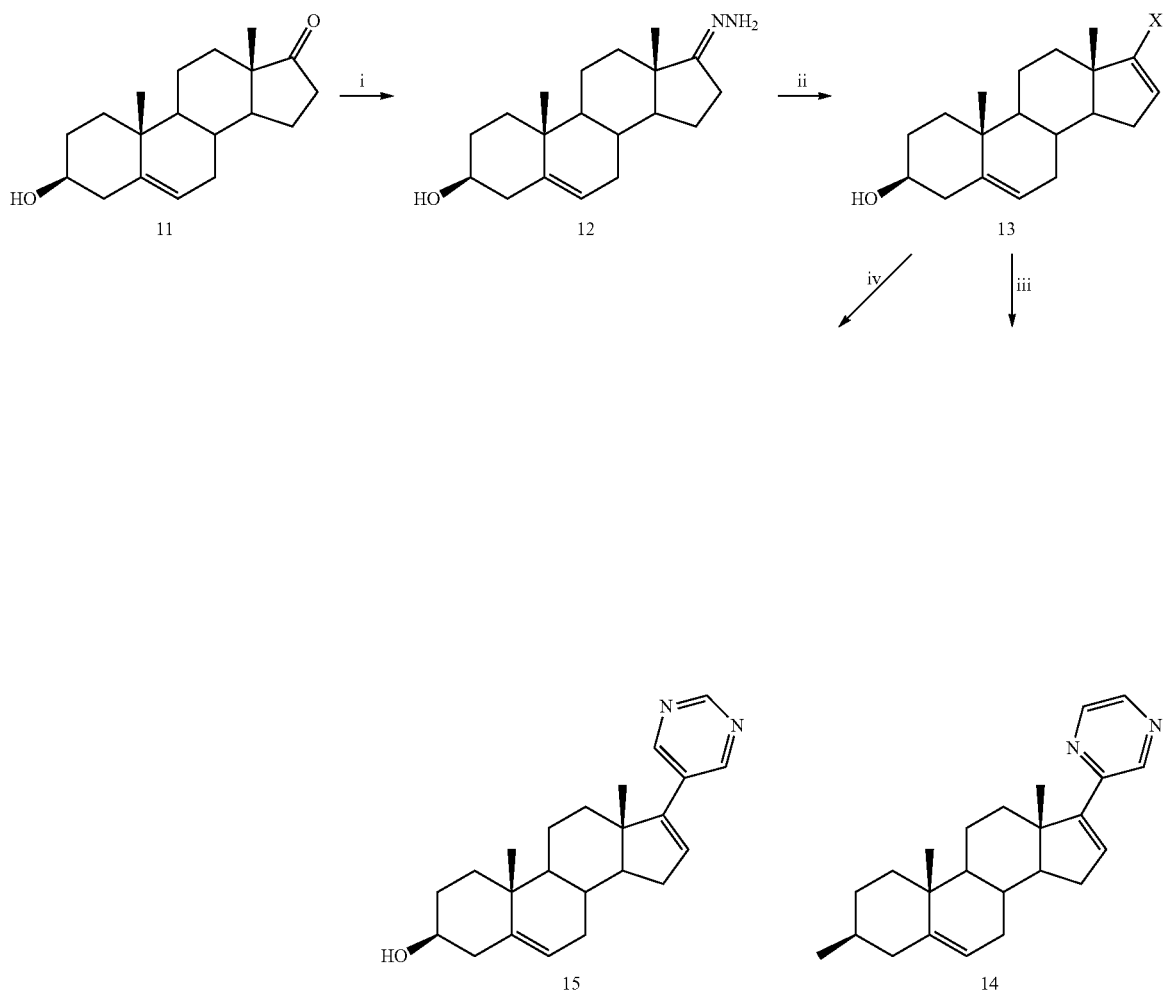
i) N₂H₄.H₂O, N₂H₄.H₂SO₄, EtOH;
ii) I₂TTHF, TG;
iii) (2-tributylstannyl pyrazine/Pd(PPh3)4;
iv) (5-tributylstannyl)pyrimidine/Pd(PPh3)₄
Scheme 3. Synthesis of glycine dipeptide prodrug of Compound 5
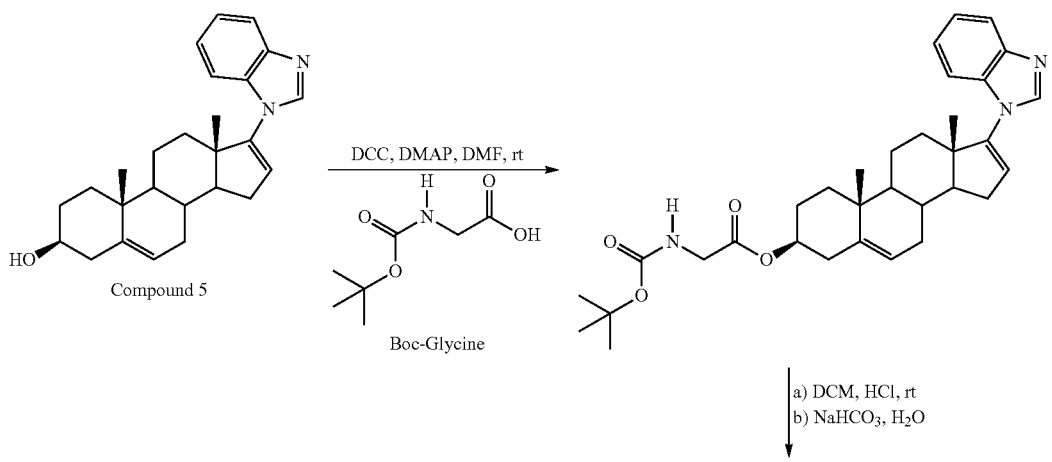
a) DCM, HCl, rt
b) NaHCO₃, H₂O -continued
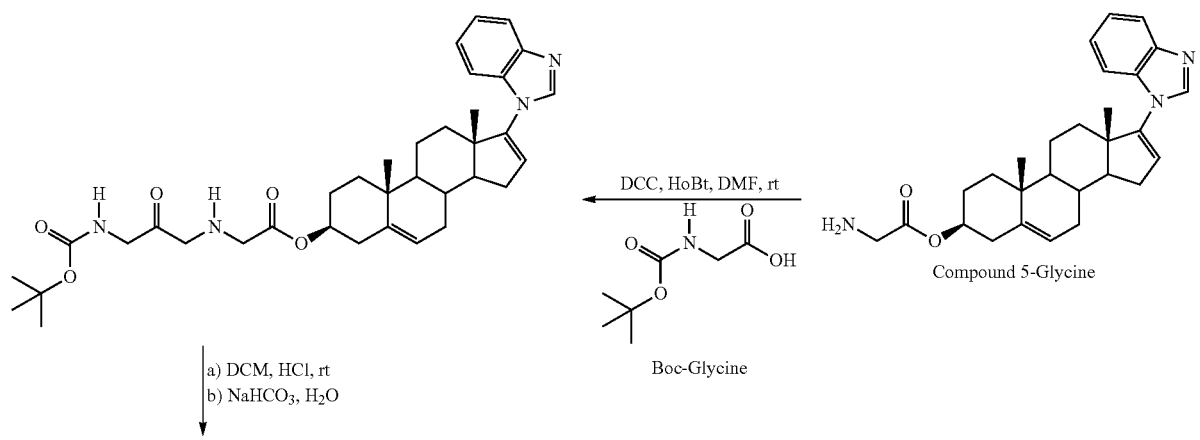
Compound 5-Glycine
a) DCM, HCl, rt
b) NaHCO₃, H₂O
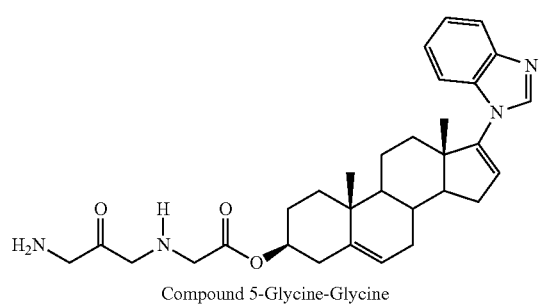
Compound 5-Glycine-Glycine
Scheme 4. Synthesis of valine prodrug of Compound 5
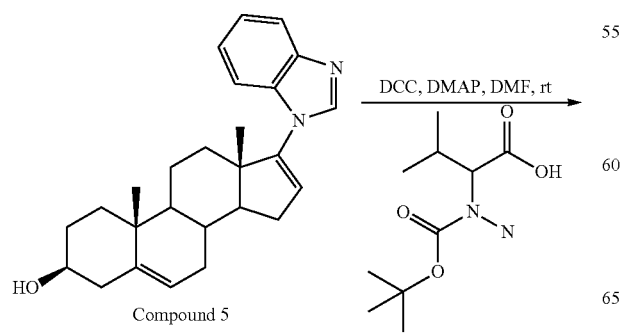
Compound 5

35
-continued
36
-continued
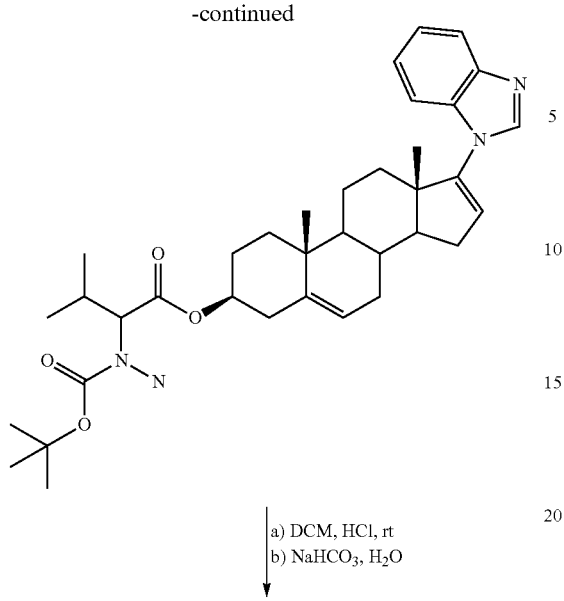
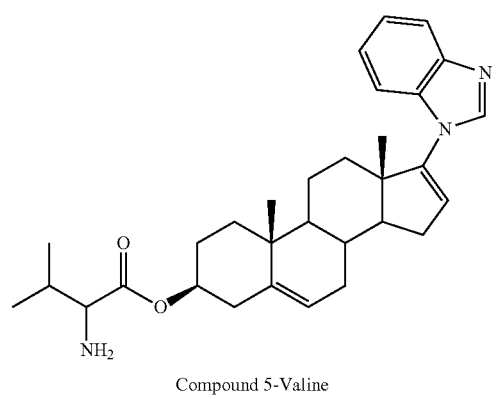
Compound 5-Valine
Scheme 5. Synthesis of glycine-valine dipeptide prodrug of Compound 5
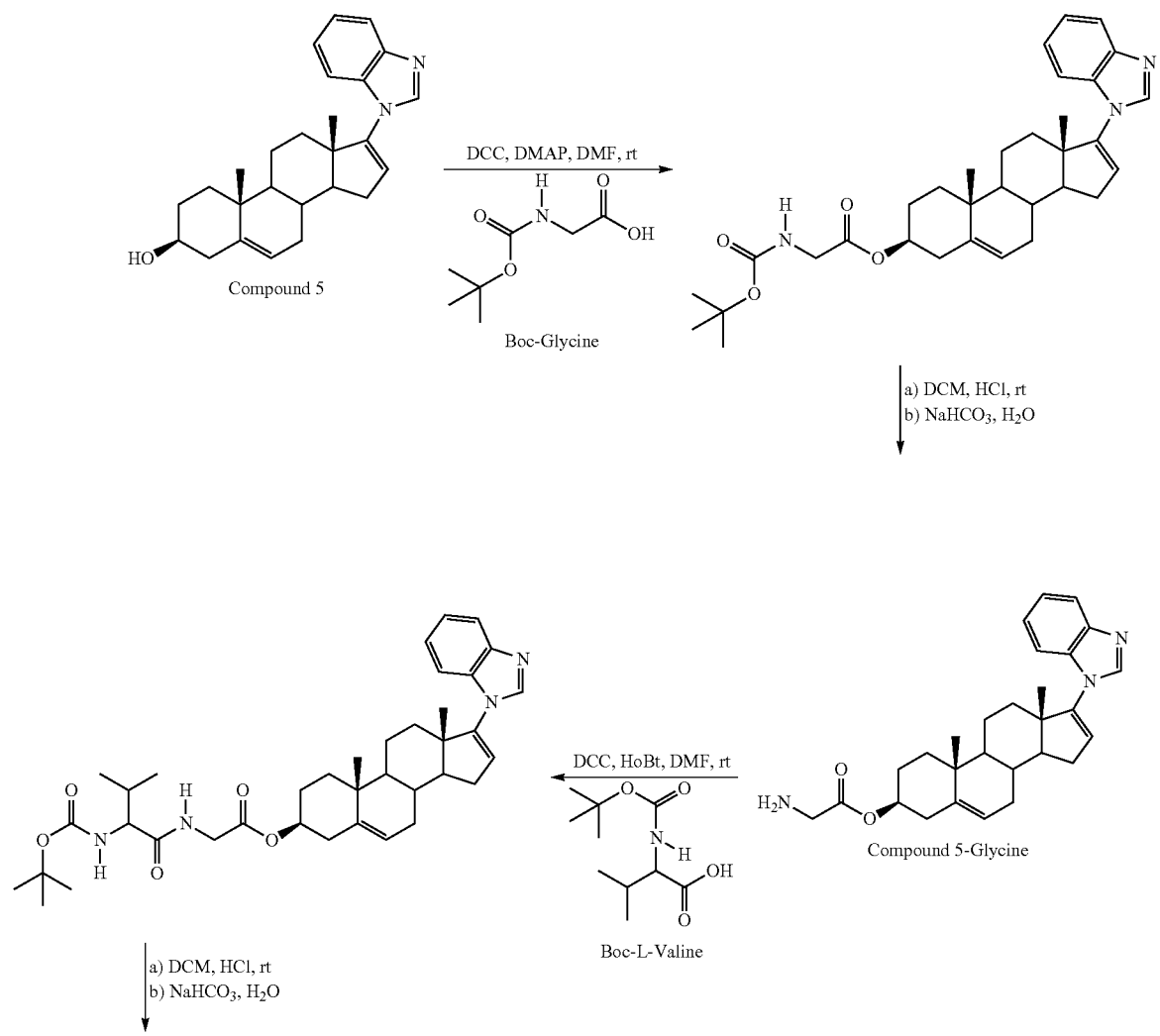

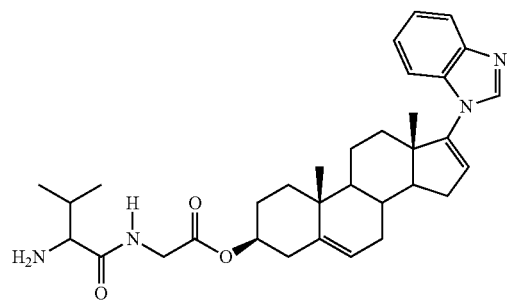
Compound 5-Glycine-Valine
Scheme 6. Synthesis of lysine prodrug of Compound 5
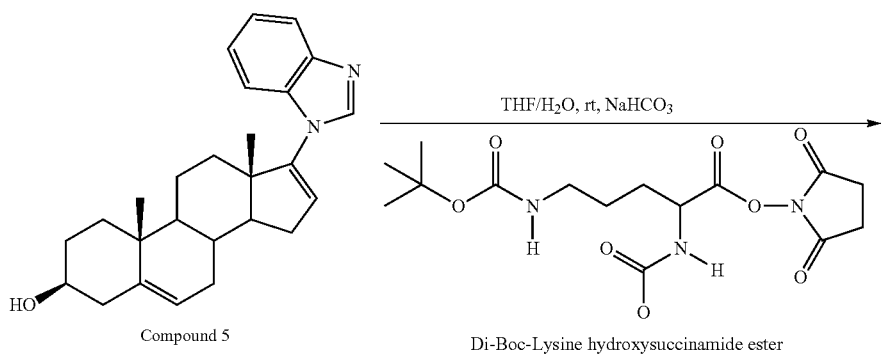
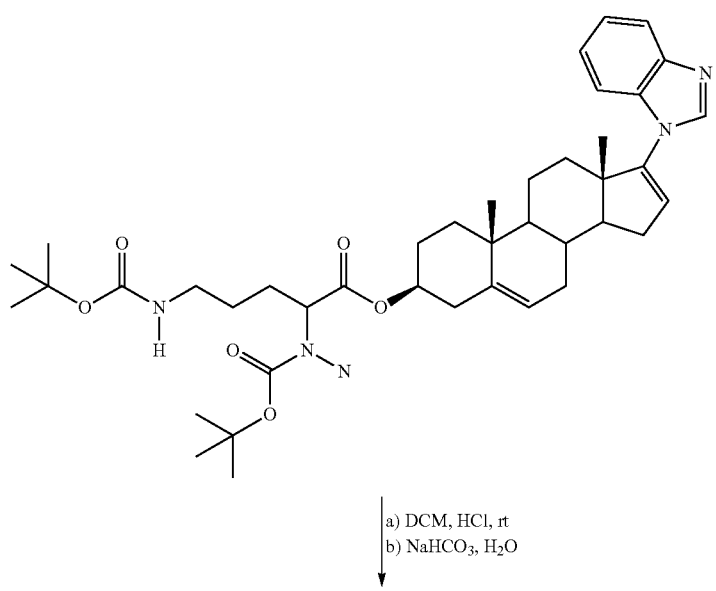
a) DCM, HCl, rt
b) NaHCO$_3$, H$_2$O

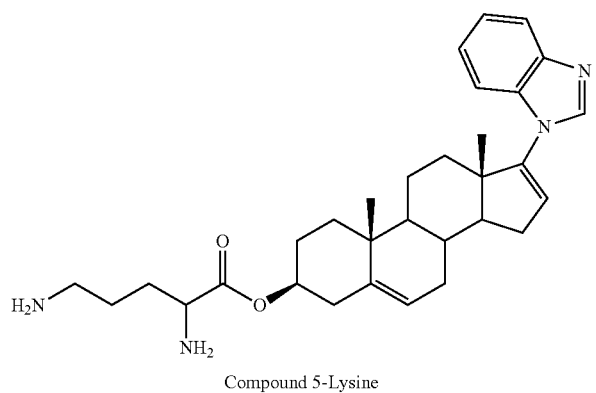
Compound 5-Lysine
Scheme 7. Synthesis of aspartic acid prodrug of Compound 5
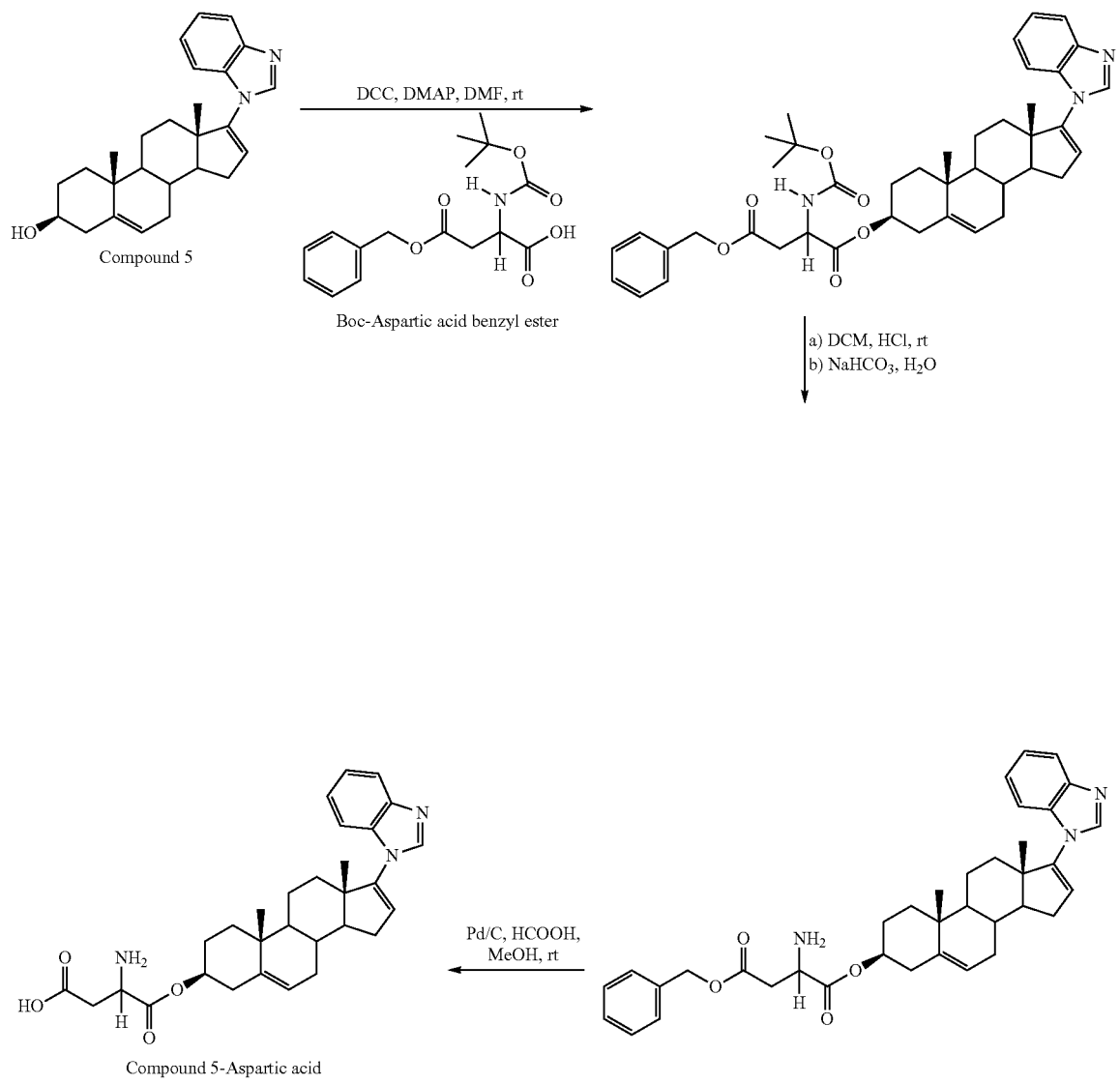
Compound 5-Aspartic acid Scheme 8. Synthesis of succinate prodrug of Compound 5
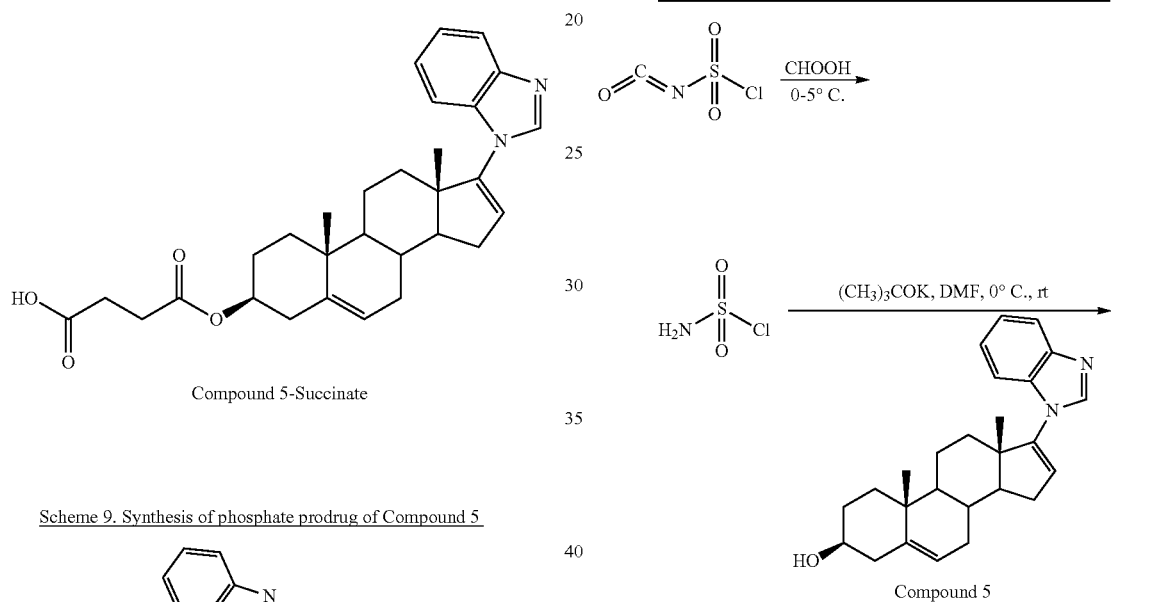
Scheme 9. Synthesis of phosphate prodrug of Compound 5
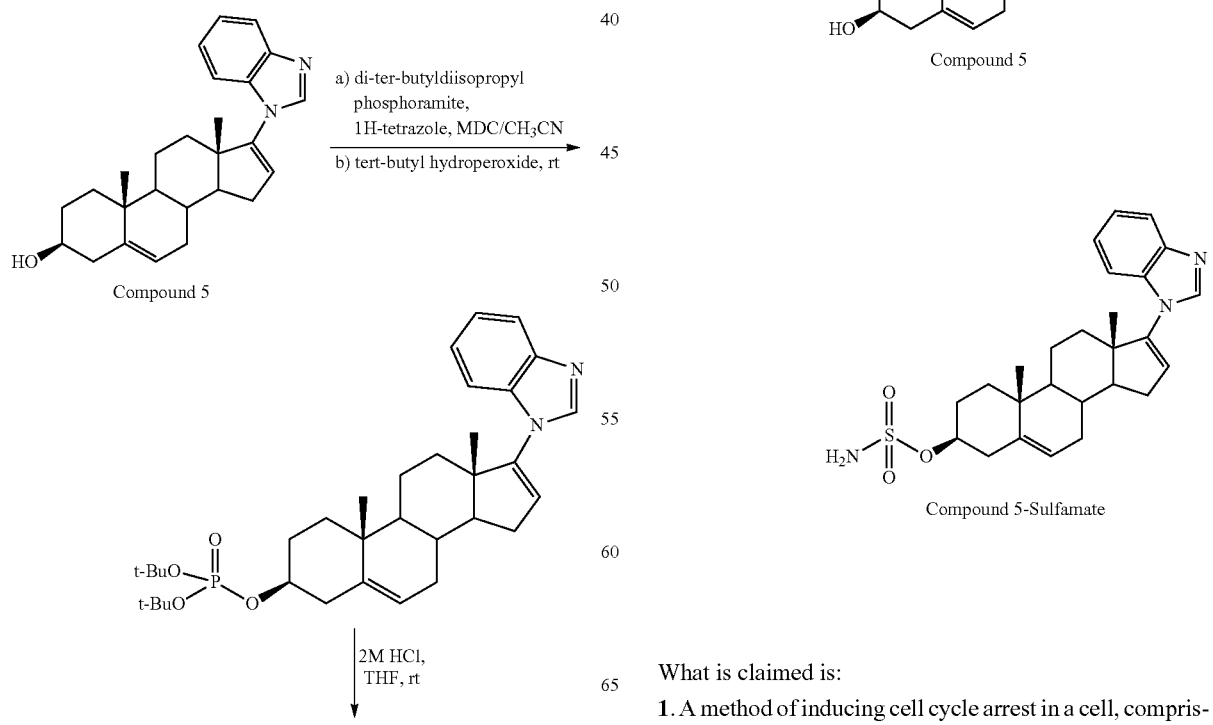
Scheme 10. Synthesis of sulfamate prodrug of Compound 5
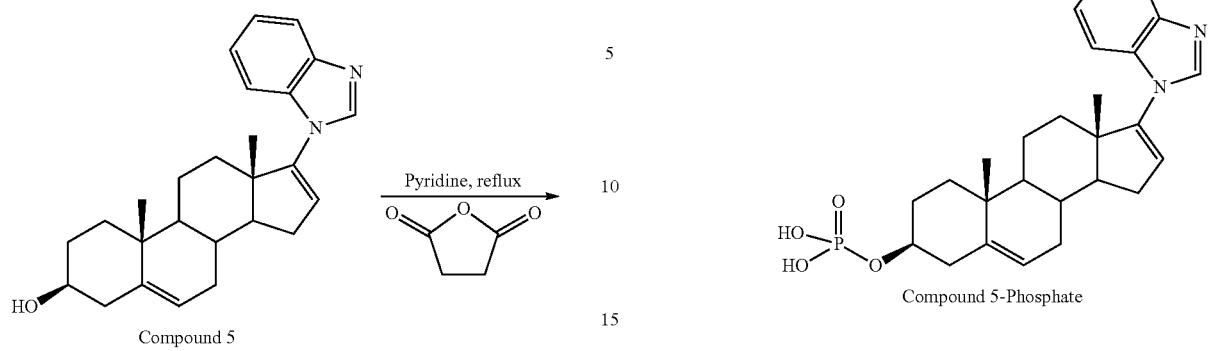
What is claimed is:
1. A method of inducing cell cycle arrest in a cell, comprising administering to the cell an amount of Compound 5:

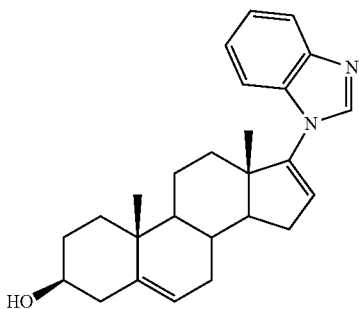 [SMILES: C[C@]12CC[C@H](O)CC1=CCC1C2CC[C@]2(C)C(n3cnc4ccccc43)=CCC12]

wherein the amount of Compound 5 is sufficient to induce cell cycle arrest.

2. The method of claim 1, wherein the cell cycle arrest is evidenced by downregulation of Cyclin D1 protein expression, downregulation of cyclin E2 mRNA, induction of G1/G0 growth arrest, downregulation of genes involved in cell cycle progression, or any combination thereof.

3. The method of claim 2, wherein the G1/G0 growth arrest is evidenced by FACS analysis of DNA content.

4. The method of claim 1, wherein the cell is a prostate cell.

5. The method of claim 4, wherein the prostate cell is a cultured cell.

6. The method of claim 5, wherein the cultured cell is a PC3 cell.

7. The method of claim 1, wherein the cell originates from a prostate hyperplasia, prostate cancer, breast cancer, or other urogenital cancer.

8. The method of claim 1, wherein the amount of compound 5 sufficient to induce cell cycle arrest is 20 μM of compound 5.

9. The method of claim 1, wherein the induction of cell cycle arrest is associated with an increase in intracellular calcium levels in the cell.

10. The method of claim 1, wherein the compound is formulated as a pharmaceutical composition.

11. The method of claim 10, wherein the pharmaceutical composition is formulated for oral administration.

12. The method of claim 11, wherein the pharmaceutical composition is formulated as a capsule, sachet, or tablet.

13. The method of claim 1, wherein the amount administered is about 1 mg to about 500 mg per day.

14. The method of claim 1, comprising co-administering to the prostate cell an additional cancer therapy and/or drug.

15. The method of claim 14, wherein the additional cancer therapy and/or drug comprises an anti-androgen, a CYP17 inhibitor, a drug that prevent adrenal glands from making androgens, and/or a leutenizing hormone-releasing hormone agonist.

16. The method of claim 15, wherein the anti-androgen is flutamide or nilutamide.

17. The method of claim 15, wherein the CYP17 inhibitor is abiraterone.

18. The method of claim 15, wherein the leutenizing hormone-releasing hormone agonist is leuprolide, goserelin, or buserelin.

19. The method of claim 15, wherein the drug that prevent adrenal glands from making androgens is ketoconazole or amino glutethimide.

20. The method of claim 1, wherein the administering is performed ex vivo.

\* \* \* \* \*